United States Patent [19]

Iwata et al.

[11] Patent Number: 4,997,943

[45] Date of Patent: Mar. 5, 1991

[54] QUINOLINE-3-CARBOXYLIC ACID DERIVATIVES

[75] Inventors: Masayuki Iwata, Tokyo; Tomio Kimura; Yoshimi Fujihara, both of Ube; Tetsushi Katsube, Ube, all of Japan

[73] Assignees: Sankyo Company Limited, Tokyo; Ube Indusstries Limited, Ube, both of Japan

[21] Appl. No.: 33,066

[22] Filed: Mar. 31, 1987

[30] Foreign Application Priority Data

Mar. 31, 1986 [JP] Japan .................................. 61-74064

[51] Int. Cl.$^5$ ............................................ C07D 101/02
[52] U.S. Cl. ..................... 544/363; 540/200; 540/364; 540/575; 544/58.6; 544/69; 544/128; 544/229; 546/13; 546/156
[58] Field of Search ........................ 544/363; 514/254

[56] References Cited

U.S. PATENT DOCUMENTS 4,638,067 1/1987 Culbertson et al. ................. 546/156

FOREIGN PATENT DOCUMENTS 0078362 5/1983 European Pat. Off. .
0106489 4/1984 European Pat. Off. .
0153163 8/1985 European Pat. Off. .

OTHER PUBLICATIONS

Masuzawa et al., "Chemical Abstracts", vol. 108, 1987, col. 108: 75232j.

*Primary Examiner*—Glennon H. Hollrah
*Assistant Examiner*—James H. Turnipseed
*Attorney, Agent, or Firm*—Frishauf, Holtz, Goodman & Woodward

[57] ABSTRACT

Compounds of formula (I):

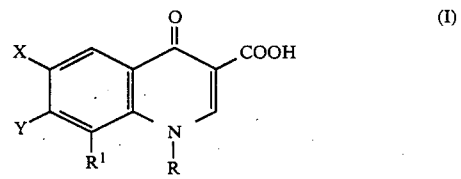

(in which $R^1$ is alkoxy, R is alkyl, haloalkyl, alkylamino, cycloalkyl or optionally substituted phenyl, X is chlorine or fluorine and Y is selected from certain specific heterocycles) have excellent antibacterial activity. They may be prepared by introducing the group represented by Y into the corresponding compound in which Y is replaced by a halogen atom.

4 Claims, No Drawings

QUINOLINE-3-CARBOXYLIC ACID DERIVATIVES

BACKGROUND TO THE INVENTION

The present invention relates to a series of novel quinoline-carboxylic acid derivatives which have been found to have valuable and powerful antibacterial activity. The invention also provides compositions containing these compounds, methods of using them and processes for preparing them.

The compounds of the present invention are 1-substituted-4-oxo-6-(fluoro or chloro)-7-(optionally substituted heterocyclic)-8-alkoxy-quinoline-3-carboxylic acid derivatives.

It is an unfortunate fact of modern medicine that many infectious bacteria are gradually developing resistance to the antibiotics commonly used to treat infection caused by them, with the result that known antibacterial agents are increasingly becoming of limited effectiveness. There is, therefore, a continuing need to develop new antibacterial agents, which may, even if only for a restricted period, be effective against infectious bacteria. Most of the common antibacterial agents in present day use were originally developed from fermentation products, although some are of wholly synthetic origin.

There have been proposals to use certain 4-oxoquinoline-3-carboxylic acid derivatives as antibacterial agents. For example, European Patent Publication No. 78 362 discloses a limited class of 1-cyclopropyl-6-fluoro-1,4-dihydro-4-oxo-7-(1-piperazinyl)quinoline-3-carboxylic acid derivatives, in which the piperazinyl group is unsubstituted or has a methyl, ethyl or β-hydroxyethyl substituent at the 4-position. These compounds resemble certain of those of the present invention, except that they lack the 8-alkoxy group which has been found to be critical to the compounds of the present invention.

European Patent Publications No. 106 489 and No. 153 163 disclose classes of quinoline derivatives, including amongst many others, a few 1-substituted-4-oxo-1,4-dihydro-6-halo-7-(optionally substituted heterocyclic)-8-substituted-quinoline-3-carboxylic acid derivatives, of which in some the 8-substituent is an alkoxy group, and which, in this respect, resemble the compounds of the present invention. However, these prior art compounds differ from those of the present invention in the nature of the 7-substituent.

Of the compounds disclosed in European Patent Publication No. 78 362, one, namely Norfloxacin, whose systematic name is 1-ethyl-6-fluoro-1,4-dihydro-4-oxo-7-(1-piperazinyl)-quinoline-3-carboxylic acid, is disclosed in The Merck Index Tenth Edition, published in 1983, monograph number 6541. In common with the other compounds of European Patent Publication No. 78 362, this lacks the critical 8-alkoxy substituent of the present invention.

We have surprisingly found that the combination of a limited class of 8-alkoxy substituents with certain limited and highly specific classes of heterocyclic substituent at the 7-position leads to the production of compounds which have unexpectedly good antibacterial activities, in many cases far surpassing those of the prior art compounds. In particular, the compounds of the present invention have surprisingly good activity against several strains of bacteria against which the known compounds are ineffective or are effective only at high concentrations, for example *Staphylococcus aureus* 535, *Enterococcus faecalis* 681 and *Escherichia coli* 609.

BRIEF SUMMARY OF INVENTION

It is, therefore, an object of the present invention to provide a series of 1-4-dihydro-4-oxo-quinoline-3-carboxylic acid derivatives which have exceptional antibacterial activity.

It is a further object of the invention to provide pharmaceutical compositions containing such a quinoline derivative as an antibacterial agent.

It is a still further object of the present invention to provide methods for the treatment or prophylaxis of bacterial infections in animals (including human beings) by the administration thereto of such a quinoline derivative.

The compounds of the invention may be represented by the formula (I), in which, for the avoidance of doubt, the numbering system employed herein is shown on the quinoline ring system:

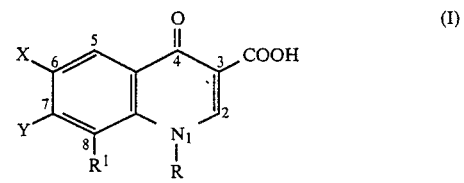

in which:

R represents a $C_1$–$C_3$ alkyl group, a $C_1$–$C_3$ alkyl group having at least one halogen substituent, a $C_1$–$C_3$ alkylamino group, a $C_3$–$C_6$ cycloalkyl group, a phenyl group or a phenyl group having at least one substituent selected from the group consisting of substituents (a), defined below;

$R^1$ represents a $C_1$–$C_3$ alkoxy group;

X represents a fluorine or chlorine atom;

Y represents:

(i) a group of formula (i):

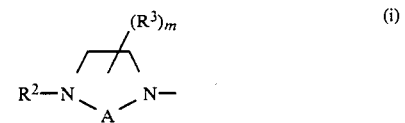

in which:

$R^2$ represents a hydrogen atom, a $C_1$–$C_4$ alkyl group, a substituted $C_1$–$C_4$ alkyl group having at least one substituent selected from the group consisting of substituents (b), defined below, a $C_1$–$C_4$ aliphatic acyl group or an aralkyl group;

$R^3$ represents a hydrogen atom or a $C_1$–$C_3$ alkyl group;

A represents a group of formula —$(CH_2)_2$—, —$(CH_2)_3$— or —$COCH_2$—; and m represents the integer 1 or 2;

(ii) a group of formula (ii):

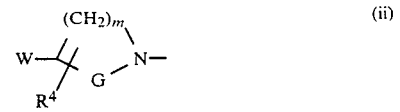

in which:

$R^4$ represents a hydrogen atom, a $C_1$–$C_3$ alkyl group, a hydroxy group or a $C_1$–$C_3$ alkoxy group;

W represents a hydroxy group, a $C_1$–$C_3$ alkoxy group or a group of formula $R^5R^6N$—$(CH_2)_n$—, in which n is 0 or 1 and $R^5$ and $R^6$ are independently selected from the group consisting of hydrogen atoms, $C_1$–$C_3$ alkyl groups and aralkyl groups;

G represents a group of formula —$CH_2$—, —$(CH_2)_2$— or —$(CH_2)_3$—; and m is as defined above;

(iii) a group of formula (iii):

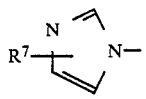

in which:

$R^7$ represents a hydrogen atom or a $C_1$–$C_3$ alkyl group; or (iv) a group of formula (iv):

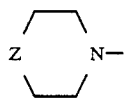

in which:

Z represents an oxygen atom or a sulfur atom;

said aralkyl groups are groups in which the alkyl part is $C_1$–$C_3$ alkyl and the aryl part is $C_6$–$C_{10}$ aryl which is unsubstituted or has at least one substituent selected from the group consisting of substituents (c), defined below;

substituents (a): $C_1$–$C_3$ alkyl groups, hydroxy groups, $C_1$–$C_3$ alkoxy groups and halogen atoms;

substituents (b): hydroxy groups, $C_2$–$C_4$ aliphatic acyloxy groups, $C_1$–$C_4$ aliphatic acyl groups, carboxy groups, $C_2$–$C_4$ alkoxycarbonyl groups, sulfo groups, amino groups, $C_2$–$C_4$ aliphatic acylamino groups, alkylamino groups in which the alkyl part is $C_1$–$C_3$ alkyl and dialkylamino groups in which each alkyl part is $C_1$–$C_3$ alkyl;

substituents (c): $C_1$–$C_3$ alkoxy groups, amino groups, alkylamino groups in which the alkyl part is $C_1$–$C_4$ alkyl and dialkylamino groups in which each alkyl part is $C_1$–$C_4$ alkyl;

and pharmaceutically acceptable salts, esters and amides thereof.

The invention also provides a pharmaceutical composition for the treatment of bacterial infections, comprising an antibacterial agent in combination with a pharmaceutically acceptable carrier or diluent, wherein the antibacterial agent is selected from the group consisting of compounds of formula (I) and pharmaceutically acceptable salts, esters and amides thereof.

The invention still further provides a method for the treatment or prophylaxis of bacterial infection comprising administering an amount of an antibacterial agent to an animal (which may be a mammal, e.g. human) sufficient to exert an antibacterial effect, wherein said antibacterial agent is selected from the group consisting of compounds of formula (I) and pharmaceutically acceptable salts, esters and amides thereof.

The invention also provides methods of preparing the compounds of the invention, which are described in more detail hereafter.

DETAILED DESCRIPTION OF INVENTION

In the compounds of the invention, where R, $R^3$, $R^4$, $R^5$, $R^6$, $R^7$ or substituents (a) represents a $C_1$–$C_3$ alkyl group, these groups may be straight or branched chain groups and examples include the methyl, ethyl, propyl and isopropyl groups, of which the methyl and ethyl groups are most preferred.

Where R represents a $C_1$–$C_3$ alkyl group having at least one halogen substituent, the halogen substituent is preferably selected from the group consisting of fluorine, chlorine, bromine and iodine atoms, more preferably fluorine and chlorine atoms. The alkyl group itself may be a straight or branched chain alkyl group and examples of such groups are given above in relation to the groups which may be represented by, inter alia, R; the alkyl group is more preferably a $C_1$ or $C_2$ alkyl group. The number of halogen substituents is limited only by the number of carbon atoms available to substitute, and the substituted alkyl group could be anything from a monohaloalkyl group to a perhaloalkyl group. In general, the most commonly available haloalkyl groups contain 1, 2 or 3 halogen atoms and, for this reason alone, such mono-, di- and tri-haloalkyl groups are preferred, but it should be borne in mind that any greater number of halogen atoms up to complete halogenation is possible. Examples of preferred haloalkyl groups include the fluoromethyl, difluoromethyl, chloromethyl, trifluoromethyl, 2-chloroethyl, 2-fluoroethyl, 2,2,2-trichloroethyl and 3-fluoropropyl groups, more preferably the 2-fluoroethyl group.

Where R represents a $C_1$–$C_3$ alkylamino group, the alkyl part may be as exemplified above in relation to the groups which may be represented by R. Specific examples include the methylamino, ethylamino, propylamino and isopropylamino groups, of which the methylamino group is most preferred.

Where R represents a cycloalkyl group, this has from 3 to 6 ring carbon atoms and examples include the cyclopropyl, cyclobutyl, cyclopentyl and cyclohexyl groups. Of these, the cyclopropyl group is preferred.

Where R represents a phenyl group, this may be unsubstituted or it may have at least one substituent selected from the group consisting of substituents (a), defined above. If it is substituted, it preferably has 1 or 2 of said substituents, and preferred examples of such substituted phenyl groups include the tolyl (p-, o- or m-tolyl), hydroxyphenyl (p-, o- or m- hydroxyphenyl), methoxyphenyl (p-, o- or m- methoxyphenyl), ethoxyphenyl (p-, o- or m- ethoxyphenyl), chlorophenyl (p-, o- or m- chlorophenyl), fluorophenyl (p-, o- or m- fluorophenyl), difluorophenyl (e.g. 2,3-, 2,4-, 2,5-, 2,6- or 3,4-fluorophenyl) groups.

Of the specific groups exemplified above for R, the following are preferred: the methyl, ethyl, 2-fluoroethyl, methylamino, p-hydroxyphenyl, p-methoxyphenyl, fluorophenyl (especially p-fluorophenyl), difluorophenyl (especially 2,4-difluorophenyl) and cyclopropyl groups. In general, the cycloalkyl groups are preferred, and so the cyclopropyl group is the most preferred group.

Where $R^1$ represents a $C_1$–$C_3$ alkoxy group, this group may be a straight or branched chain group and examples include the methoxy, ethoxy, propoxy and isopropoxy groups, of which the methoxy group is preferred.

X represents a fluorine or chlorine atom, the fluorine atom being preferred.

Where Y represents said group of formula (i) and $R^2$ represents a $C_1$–$C_4$ alkyl group, this may be a straight or branched chain group and examples include the methyl, ethyl, propyl, isopropyl, butyl, isobutyl, sec-butyl and t-butyl groups, of which the methyl and ethyl groups are most preferred. Such a group represented by $R^2$ may be substituted or unsubstituted, and, if substituted, the substituents may be selected from the group consisting of substituents (b), as exemplified elsewhere herein.

Where Y represents said group of formula (i) and $R^2$ represents a $C_1$–$C_4$ aliphatic acyl group, this may be a straight or branched chain carboxylic acyl group and may be saturated or unsaturated. It is preferably a formyl, acetyl, propionyl, acryloyl, propioloyl, methacryloyl, crotonoyl, isocrotonoyl, butyryl or isobutyryl group.

Where Y represents said group of formula (i) and $R^2$ represents an aralkyl group, the alkyl part is $C_1$–$C_3$ alkyl and the aryl part is $C_6$–$C_{10}$ aryl which is unsubstituted or has at least one substituent selected from the group consisting of substituents (c), as exemplified elsewhere herein. Examples of such aralkyl groups include the benzyl, phenethyl and phenylpropyl (especially 3-phenylpropyl) groups and the substituted analogs thereof, e.g. the p-methoxybenzyl, p-aminobenzyl, p-methylaminobenzyl or p-dimethylaminobenzyl groups.

Where Y represents said group of formula (ii) and $R^4$ and/or W represents a $C_1$–$C_3$ alkoxy group or substituent (a) or (c) represents a $C_1$–$C_3$ alkoxy group, this group may be a straight or branched chain group and examples include the methoxy, ethoxy, propoxy and isopropoxy groups, of which the $C_1$ and $C_2$ alkoxy groups, i.e. the methoxy and ethoxy groups, are preferred.

Where Y represents said group of formula (ii) and W represents said group of formula $R^5R^6N$—$(CH_2)_n$—, n is 0 or 1 and $R^5$ and $R^6$ are independently selected from the group consisting of hydrogen atoms, $C_1$–$C_3$ alkyl groups and aralkyl groups, said alkyl groups and aralkyl groups being as exemplified above.

Where Y represents said group of formula (ii), B represents said group of formula —$CH_2$—, —$(CH_2)_2$— or —$(CH_2)_3$—, said groups of formula —$CH_2$— and —$(CH_2)_2$— being more preferred.

Where Y represents said group of formula (iii) and $R^7$ represents a $C_1$–$C_3$ alkyl group, this may be as exemplified above.

Where Y represents said group of formula (iv), then this is either the morpholino group (Z=oxygen) or the perhydro-1,4-thiazin-4-yl (=thiomorpholino) group, when Z=sulfur.

Where substituent (a) represents a halogen atom, this is preferably a fluorine, chlorine, bromine or iodine atom, more preferably a fluorine atom.

Where substituent (b) represents an aliphatic acyloxy group containing from 2 to 4 carbon atoms, this may be a straight or branched chain carboxylic acyl group and may be saturated or unsaturated (the terms "saturated" and "unsaturated" referring to the carbon-carbon bonds). It is preferably an acetoxy, propionyloxy, butyryloxy or isobutyryloxy group.

Where substituent (b) represents an aliphatic acyl group containing from 1 to 4 carbon atoms, this may be a straight or branched chain carboxylic acyl group and may be saturated or unsaturated. It is preferably a formyl, acetyl, propionyl, butyryl or isobutyryl group.

Where substituent (b) represents an aliphatic acylamino group containing from 2 to 4 carbon atoms, this may be a straight or branched chain carboxylic acylamino group and may be saturated or unsaturated. It is preferably an acetamido, propionamido, butyramido or isobutyramido group.

Where substituent (b) or substituent (c) represents a mono- or di- alkylamino group in which the or each alkyl part contains from 1 to 4 carbon atoms the alkyl part may be as exemplified above in relation to $R^2$, and examples of such alkylamino groups include the methylamino, ethylamino, propylamino, isopropylamino, butylamino, isobutylamino, dimethylamino, diethylamino, dipropylamino and diisopropylamino groups.

Preferred compounds of the present invention are:

(A) Those compounds of formula (I) in which:
R represents an ethyl group, a 2-fluoroethyl group, a cyclopropyl group or a phenyl group having one or two fluorine substituents, preferably a 4-fluorophenyl or 2,4-difluorophenyl group;
$R^1$ represents a methoxy group;
X represents a fluorine atom; and
Y represents a group of formula (i):

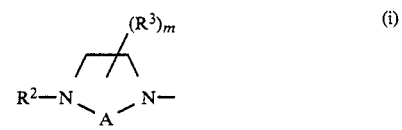

in which $R^2$, $R^3$, A and m are as defined above;
and pharmaceutically acceptable salts, esters and amides thereof.

(B) Those compounds of formula (I) in which:
R represents an ethyl group, a 2-fluoroethyl group, a cyclopropyl group, or a phenyl group having one or two fluorine substituents;
$R^1$ represents a methoxy group;
X represents a fluorine atom; and
Y represents a group of formula (ii):

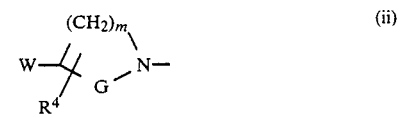

in which:
$R^4$ represents a hydrogen atom or a $C_1$–$C_3$ alkyl group;
W represents a hydroxy group;
G represents a group of formula —$CH_2$— or —$(CH_2)_2$—; and
m is as defined above;
and pharmaceutically acceptable salts, esters and amides thereof.

(C) Those compounds of formula (I) in which:
R represents an ethyl group, a 2-fluoroethyl group, a cyclopropyl group or a phenyl group having one or two fluorine substituents;
$R^1$ represents a methoxy group;
X represents a fluorine atom; and
Y represents a group of formula (ii):

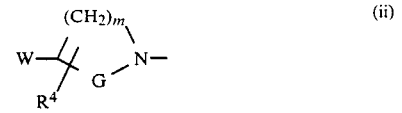

in which:
R⁴ represents a hydrogen atom, a C₁-C₃ alkyl group, a hydroxy group or a C₁-C₃ alkoxy group;
W represents a group of formula

R⁵R⁶N—(CH₂)ₙ—, in which n, R⁵ and R⁶ are as defined above;
G represents a group of formula —CH₂— or —(CH₂)₂—; and
m is as defined above;
and pharmaceutically acceptable salts, esters and amides thereof.

(D) Those compounds of formula (I) in which:
R represents an ethyl group, a 2-fluoroethyl group, a cyclopropyl group or a phenyl group having one or two fluorine substituents;
R¹ represents a methoxy group;
X represents a fluorine atom; and
Y represents a group of formula (ii):

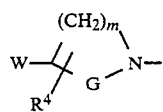

in which:
R⁴ represents a hydroxy group or a C₁-C₃ alkoxy group;
W represents a hydroxy group or a C₁-C₃ alkoxy group;
G represents a group of formula —(CH₂)₂—; and
m is 1;
and pharmaceutically acceptable salts, esters and amides thereof.

(E) Those compounds of formula (I) in which:
R represents an ethyl group, a 2-fluoroethyl group, a cyclopropyl group or a phenyl group having one or two fluorine substituents;
R¹ represents a methoxy group;
X represents a fluorine atom; and
Y represents a group of formula (iiia):

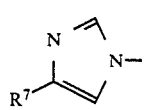

in which:
R⁷ represents a hydrogen atom or a C₁-C₃ alkyl group;
and pharmaceutically acceptable salts, esters and amides thereof.

(F) Those compounds of formula (I) in which:
R represents an ethyl group, a 2-fluoroethyl group, a cyclopropyl group or a phenyl group having one or two fluorine substituents;
R¹ represents a methoxy group;
X represents a fluorine atom; and
Y represents a group of formula (iv):

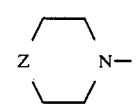

in which:
Z represents an oxygen atom or a sulfur atom;
and pharmaceutically acceptable salts, esters and amides thereof.

More preferred compounds of the present invention are:
(G) Those compounds defined in (A), (B), (C), (D), (E) and (F) above in which R represents a cyclopropyl group.

Still more preferred compounds of the present invention are:
(H) Those compounds of formula (I) in which:
R represents a cyclopropyl group;
R¹ represents a methoxy group;
X represents a fluorine atom; and
Y represents a group of formula (i):

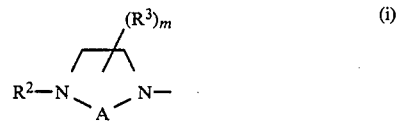

in which:
R² represents a hydrogen atom, a C₁ or C₂ alkyl group, a C₁ or C₂ aliphatic acyl group or a substituted C₁ or C₂ alkyl group having at least one hydroxy substituent;
R³ represents a hydrogen atom or a methyl group;
A group )₃— or —COCH₂—; and
m represents the integer 1 or 2;
and pharmaceutically acceptable salts, esters and amides thereof.

Further more preferred compounds of the present invention are:
(J) Those compounds of formula (I) in which:
R represents a cyclopropyl group;
R¹ represents a methoxy group;
X represents a fluorine atom; and
Y represents a group of formula (iia):

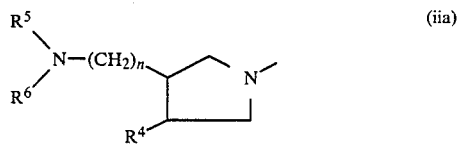

in which:
R⁴ represents a hydrogen atom, a C₁-C₃ alkyl group, a hydroxy group or a C₁-C₃ alkoxy group;
R⁵ and R⁶ are independently selected from the group consisting of hydrogen atoms, methyl groups and ethyl groups; and
n is 0 or 1;
and pharmaceutically acceptable salts, esters and amides thereof.

The compounds of the invention contain one carboxy group at the 3-position of th quinoline ring. This carboxy group may form esters, amides and salts.

Where the carboxy group is esterified, the nature of the resulting ester is not critical to the present invention. In principle, the compounds of the invention, being carboxylic acids, will form esters with any ester-forming alcohol and all such esters form part of the present invention. However, where the esters are to be employed for therapeutic purposes, it is, of course, necessary that the resulting esters should be pharmaceutically acceptable, which, as is well understood in the art, means that the esters should not have reduced activity (or unacceptably reduced activity) and should not have increased toxicity (or unacceptably increased toxicity) as compared with the free acid. However, where the ester is to be employed for other purposes, for example as an intermediate in the preparation of other compounds, even this criterion does not apply.

Examples of such esters include: $C_1$–$C_6$, more preferably $C_1$–$C_4$, alkyl esters, for example the methyl, ethyl, propyl, isopropyl, butyl, isobutyl, sec-butyl, t-butyl, pentyl and hexyl esters; aralkyl (including diarylalkyl) esters, such as the benzyl, p-nitrobenzyl and benzhydryl esters; lower aliphatic acyloxyalkyl groups, such as the acetoxymethyl or pivaloyloxymethyl groups; alkoxycarbonylalkyl esters, in which the alkoxy and alkyl parts are both $C_1$–$C_4$, especially alkoxycarbonylmethyl esters, such as the ethoxycarbonylmethyl and t-butoxycarbonylmethyl esters; alkoxycarbonyloxyalkyl esters in which the alkoxy and alkyl parts are both $C_1$–$C_4$, especially the 1- and 2-(alkoxycarbonyloxy)ethyl esters, such as the 1-(ethoxycarbonyloxy)ethyl, 1-(isopropoxycarbonyloxy)ethyl, 2-methoxycarbonyloxyethyl, 2-ethoxycarbonyloxyethyl and 2-t-butoxycarbonyloxyethyl esters; and other specific esters, such as the phthalidyl, substituted phthalidyl, phenacyl, substituted phenacyl (e.g. p-nitrophenacyl), (5-phenyl-2-oxo-1,3-dioxolen-4-yl)methyl and (5-methyl-2-oxo-1,3-dioxolen-4-yl)methyl esters.

Likewise, where the carboxy group has formed an amide, the precise nature of the amide is not critical, provided that, where the amide is to be used for therapeutic purposes, the resulting amide is pharmaceutically acceptable. Accordingly, the carboxy group can be replaced by a carbamoyl group or a substituted carbamoyl group, preferably an alkylcarbamoyl or dialkylcarbamoyl group in which the or each alkyl group is a $C_1$–$C_3$ alkyl group (e.g. as defined above in relation to R), for example a methylcarbamoyl, ethylcarbamoyl, dimethylcarbamoyl or diethylcarbamoyl group.

The carboxy group may also form salts with appropriate bases. The nature of such salts is likewise not critical, provided that, where they are to be used for therapeutic purposes, the salts are pharmaceutically acceptable. Examples of salts with bases include: salts with metals, especially alkali metals and alkaline earth metals, such as the lithium, sodium, potassium, calcium and magnesium salts; the ammonium salt; salts with organic amines, such as cyclohexylamine, diisopropylamine or triethylamine; and salts with basic amino acids, such as lysine or arginine.

The compounds of the invention contain a basic nitrogen atom and hence can also form acid addition salts. The nature of such salts is likewise not critical to the present invention, except that, where the salts are to be used for therapeutic purposes, they must be pharmaceutically acceptable. A wide variety of acids may be employed to form such salts and representative examples of such acids include: mineral acids, such as hydrochloric acid, hydrobromic acid, hydroiodic acid, phosphoric acid, metaphosphoric acid, nitric acid or sulfuric acid; organic carboxylic acids, such as acetic acid, oxalic acid, tartaric acid, citric acid, benzoic acid, glycolic acid, gluconic acid, glucuronic acid, succinic acid, maleic acid or fumaric acid; and organic sulfonic acids, such as methanesulfonic acid, benzenesulfonic acid or p-toluenesulfonic acid. Such acid addition salts may be prepared by conventional methods.

The compounds of the invention may also exist in the form of hydrates and these likewise form part of the present invention.

Examples of specific compounds of the invention are given in the following formulae (I-1) to (I-4), in which the substituents are as defined in the corresponding one of Tables 1 to 4 [i.e. Table 1 relates to formula (I-1), Table 2 relates to formula (I-2) and so on]. The compounds of the invention are hereinafter, where appropriate, identified by the numbers appended to them in these Tables. In the Tables, the following abbreviations are used:

| | |
|---|---|
| Ac | acetyl |
| Azt | azetidinyl |
| Bz | benzyl |
| Et | ethyl |
| Etc | ethoxycarbonyl |
| Fo | formyl |
| Hip | homopiperazinyl |
| | (= perhydro-1,4-diazepinyl) |
| Me | methyl |
| Mor | morpholino |
| Ph | phenyl |
| Pip | piperidyl |
| Piz | piperazinyl |
| Pr | propyl |
| cPr | cyclopropyl |
| *Pr* | isopropyl |
| Pyrd | pyrrolidinyl |
| Sfo | sulfo |
| Thz | perhydro-1,4-thiazin-4-yl |
| | (= thiomorpholino) |

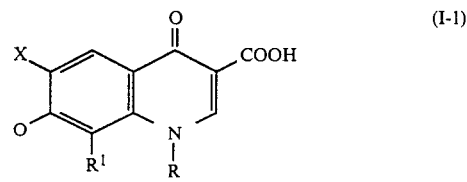
(I-1)

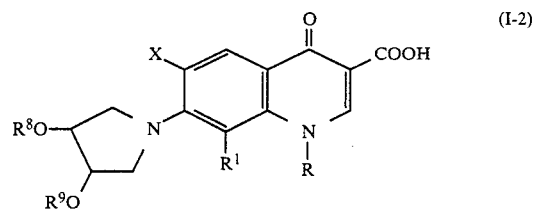
(I-2)

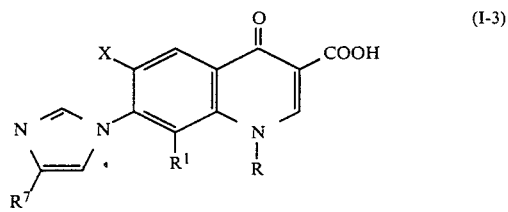
(I-3)

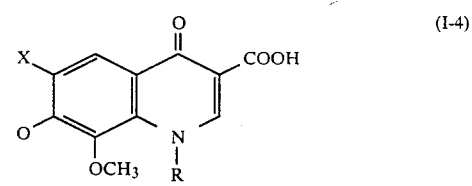
(I-4)

TABLE 1

| CPd. No. | R¹ | X | R | D |
|---|---|---|---|---|
| 1-1 | MeO | F | cPr | 1-Piz |
| 1-2 | MeO | F | cPr | 3-Me-1-Piz |
| 1-3 | MeO | F | cPr | 3,5-diMe-1-Piz |
| 1-4 | MeO | F | cPr | 2,5-diMe-1-Piz |
| 1-5 | MeO | F | cPr | 3,3-diMe-1-piz |
| 1-6 | MeO | F | cPr | 4-Me-1-Piz |
| 1-7 | MeO | F | cPr | 3,4-diMe-1-Piz |
| 1-8 | MeO | F | cPr | 3,4,5-triMe-1-Piz |
| 1-9 | MeO | F | cPr | 2,4,5-triMe-1-Piz |
| 1-10 | MeO | F | cPr | 4-Et-1-Piz |
| 1-11 | MeO | F | cPr | 4-(2HOEt)-1-Piz |
| 1-12 | MeO | F | cPr | 4-(2-AcOEt)-1-Piz |
| 1-13 | MeO | F | cPr | 4-(2-NH₂Et)-1-Piz |
| 1-14 | MeO | F | cPr | 4-(2-AcNHEt)-1-Piz |
| 1-15 | MeO | F | cPr | 4-(2-NMe₂Et)-1-Piz |
| 1-16 | MeO | F | cPr | 4-(p-NH₂Bz)-1-Piz |
| 1-17 | MeO | F | cPr | 4-Fo-1-Piz |
| 1-18 | MeO | F | cPr | 4-Ac-1-Piz |
| 1-19 | MeO | F | cPr | 4-AcCH₂-1-Piz |
| 1-20 | MeO | F | cPr | 4-(HOOC-CH₂)-1-Piz |
| 1-21 | MeO | F | cPr | 4-(EtcCH₂)-1-Piz |
| 1-22 | MeO | F | cPr | 4-(Sfo-CH₂)-1-Piz |
| 1-23 | MeO | F | cPr | 1-Hip |
| 1-24 | MeO | F | cPr | 4-Me-1-Hip |
| 1-25 | MeO | F | cPr | 3-oxo-1-Piz |
| 1-26 | MeO | F | cPr | 4-Me-1-oxo-1-Piz |
| 1-27 | MeO | Cl | cPr | 1-Piz |
| 1-28 | MeO | Cl | cPr | 3-Me-1-Piz |
| 1-29 | MeO | Cl | cPr | 4-Me-1-Piz |
| 1-30 | MeO | Cl | cPr | 4-(2-HOEt)-1-Piz |
| 1-31 | MeO | Cl | cPr | 4-(p-NH₂Bz)-1-Piz |
| 1-32 | MeO | Cl | cPr | 4-Fo-1-Piz |
| 1-33 | MeO | Cl | cPr | 4-Me-1-Hip |
| 1-34 | MeO | Cl | cPr | 3-oxo-1-Piz |
| 1-35 | EtO | F | cPr | 1-Piz |
| 1-36 | EtO | F | cPr | 3-Me-1-Piz |
| 1-37 | EtO | F | cPr | 4-Me-1-Piz |
| 1-38 | EtO | F | cPr | 4-(2-HOEt)-1-Piz |
| 1-39 | EtO | F | cPr | 4-Ac-1-Piz |
| 1-40 | EtO | F | cPr | 4-Me-1-Hip |
| 1-41 | EtO | Cl | cPr | 1-Piz |
| 1-42 | EtO | Cl | cPr | 4-Me-1-Piz |
| 1-43 | MeO | F | Et | 4-Fo-1-Piz |
| 1-44 | MeO | F | Et | 4-Ac-1-Piz |
| 1-45 | MeO | F | Et | 4-(AcCH₂)-1-Piz |
| 1-46 | MeO | F | Et | 4-(2-HOEt)-1-Piz |
| 1-47 | MeO | F | Et | 4-(2-NH₂Et)-1-Piz |
| 1-48 | MeO | F | 2-FEt | 4-Fo-1-Piz |
| 1-49 | MeO | F | 2-FEt | 4-Ac-1-Piz |
| 1-50 | MeO | F | 2-FEt | 4-(AcCh₂)-1-Piz |
| 1-51 | MeO | F | 2-FEt | 4-(2-HOEt)-1-Piz |
| 1-52 | MeO | F | 2-FEt | 4-(2-NH₂Et)-1-Piz |
| 1-53 | MeO | F | 4-FPh | 1-Piz |
| 1-54 | MeO | F | 4-FPh | 3-Me-1-Piz |
| 1-55 | MeO | F | 4-FPh | 3,5-diMe-1-Piz |
| 1-56 | MeO | F | 4-FPh | 4-Me-1-Piz |
| 1-57 | MeO | F | 4-FPh | 3,4-diMe-1-piz |
| 1-58 | MeO | F | 4-FPh | 4-Et-1-Piz |
| 1-59 | MeO | F | 4-FPh | 4-(2-HOEt)-1-Piz |
| 1-60 | MeO | F | 4-FPh | 4-(2-NH₂Et)-1-Piz |
| 1-61 | MeO | F | 4-FPh | 1-Hip |
| 1-62 | MeO | F | 4-FPh | 4-Me-1-Hip |
| 1-63 | MeO | F | 2,4-diFPh | 1-Piz |
| 1-64 | MeO | F | 2,4-diFPh | 3-Me-1-Piz |
| 1-65 | MeO | F | 2,4-diFPh | 3,5-diMe-1-Piz |
| 1-66 | MeO | F | 2,4-diFPh | 4-Me-1-Piz |
| 1-67 | MeO | F | 2,4-diFPh | 3,4-diMe-1-Piz |
| 1-68 | MeO | F | 2,4-diFPh | 4-Et-1-Piz |
| 1-69 | MeO | F | 2,4-diFPh | 4-(2-HOEt)-1-Piz |
| 1-70 | MeO | F | 2,4-diFPh | 4-(2-NH₂Et)-1-Piz |
| 1-71 | MeO | F | 2,4-diFPh | 1-Hip |
| 1-72 | MeO | F | 2,4-diFPh | 4-Me-1-Hip |
| 1-73 | MeO | F | 4-HOPh | 1-Piz |
| 1-74 | MeO | F | 4-HOPh | 3-Me-1-Piz |
| 1-75 | MeO | F | 4-HOPh | 4-Me-1-Piz |
| 1-76 | MeO | F | 4-MeOPh | 1-Piz |
| 1-77 | MeO | F | 4-MeOPh | 3-Me-1-Piz |
| 1-78 | MeO | F | 4-MeOPh | 4-Me-1-Piz |
| 1-79 | MeO | F | cPr | 3-HO-1-Azt |
| 1-80 | MeO | F | cPr | 3-HO-1-Pyrd |
| 1-81 | MeO | F | cPr | 3-HO-1-Pip |
| 1-82 | MeO | F | cPr | 4-HO-1-Pip |
| 1-83 | MeO | F | cPr | 3-HO-4-Me-1-Pyrd |
| 1-84 | MeO | F | cPr | 4-HO-3-Me-1-Pip |
| 1-85 | MeO | Cl | cPr | 4-HO-1-Pyrd |
| 1-86 | MeO | Cl | cPr | 3-HO-1-Pip |
| 1-87 | MeO | Cl | cPr | 4-HO-1-Pip |
| 1-88 | MeO | F | Me | 3-HO-1-Azt |
| 1-89 | MeO | F | Et | 3-HO-1-Azt |
| 1-90 | MeO | F | Me | 3-HO-1-Pyrd |
| 1-91 | MeO | F | Et | 3-HO-1-Pyrd |
| 1-92 | MeO | F | Et | 3-HO-1-Pip |
| 1-93 | MeO | F | Et | 4-HO-1-Pip |
| 1-94 | MeO | F | 2-FEt | 3-HO-1-Azt |
| 1-95 | MeO | F | 2-FEt | 3-HO-1-Pyrd |
| 1-96 | MeO | F | 2-FEt | 3-HO-1-Pip |
| 1-97 | MeO | F | 2-FEt | 4-HO-1-Pip |
| 1-98 | MeO | F | MeNH— | 3-HO-1-Pyrd |
| 1-99 | MeO | F | MeNH— | 3-HO-1-Pip |
| 1-100 | MeO | F | MeNH— | 4-HO-1-Pip |
| 1-101 | MeO | F | 4-FPh | 3-HO-1-Azt |
| 1-102 | MeO | F | 4-FPh | 3-HO-1-Pyrd |
| 1-103 | MeO | F | 4-FPh | 4-HO-1-Pip |
| 1-104 | MeO | F | 4-FPh | 3-HO-1-Pip |
| 1-105 | MeO | F | 2,4-diFPh | 3-HO-1-Azt |
| 1-106 | MeO | F | 2,4-diFPh | 3-HO-1-Pyrd |
| 1-107 | MeO | F | 2,4-diFPh | 4-HO-1-Pip |
| 1-108 | MeO | F | 2,4-diFPh | 3-HO-1-Pip |
| 1-109 | MeO | F | 4-MeOPh | 3-HO-1-Azt |
| 1-110 | MeO | F | 4-MeOPh | 3-HO-1-Pyrd |
| 1-111 | MeO | F | 4-MeOPh | 4-HO-1-Pip |
| 1-112 | MeO | F | 4-MeOPh | 3-HO-1-Pip |
| 1-113 | MeO | F | cPr | 3-NH₂-1-Azt |
| 1-114 | MeO | F | cPr | 3-MeNH-1-Azt |
| 1-115 | MeO | F | cPr | 3-EtNH-1-Azt |
| 1-116 | MeO | F | cPr | 3-NMe₂-1-Azt |
| 1-117 | MeO | F | cPr | 3-NH₂-2-Me-1-Azt |
| 1-118 | MeO | F | cPr | 3-MeNH-2-Me-1-Azt |
| 1-119 | MeO | F | cPr | 3-EtNH-2-Me-1-Azt |
| 1-120 | MeO | F | cPr | 3-NMe₂-2-Me-1-Azt |
| 1-121 | MeO | F | cPr | 3-(NH₂Me)-1-Azt |
| 1-122 | MeO | F | cPr | 3-(MeNHMe)-1-Azt |
| 1-123 | MeO | F | cPr | 3-(EtNHMe)-1-Azt |
| 1-124 | MeO | F | cPr | 3-(NMe₂.Me)-1-Azt |
| 1-125 | MeO | F | cPr | 3-NH₃-1-Pyrd |
| 1-126 | MeO | F | cPr | 3-MeNH-1-Pyrd |
| 1-127 | MeO | F | cPr | 3-EtNH-1-Pyrd |
| 1-128 | MeO | F | cPr | 3-NMe₂-1-Pyrd |
| 1-129 | MeO | F | cPr | 3-N(Me)(Et)-1-Pyrd |
| 1-130 | MeO | F | cPr | 3-NH₂-4-Me-1-Pyrd |
| 1-131 | MeO | F | cPr | 3-MeNH-4-Me-1-Pyrd |
| 1-132 | MeO | F | cPr | 3-EtNH-4-Me-1-Pyrd |
| 1-133 | MeO | F | cPr | 3-NMe₂-4-Me-1-Pyrd |
| 1-134 | MeO | F | cPr | 4-NH₂-2-Me-1-Pyrd |
| 1-135 | MeO | F | cPr | 4-MeNH-2-Me-1-Pyrd |
| 1-136 | MeO | F | cPr | 4-NMe₂-2-Me-1-Pyrd |
| 1-137 | MeO | F | cPr | 3-(NH₂Me)-1-Pyrd |
| 1-138 | MeO | F | cPr | 3-(MeNHMe)-1-Pyrd |
| 1-139 | MeO | F | cPr | 3-(EtNHMe)-1-Pyrd |
| 1-140 | MeO | F | cPr | 3-(NMe₂.Me)-1-Pyrd |
| 1-141 | MeO | F | cPr | 3-NH₂-4-HO-1-Pyrd |
| 1-142 | MeO | F | cPr | 3-MeNH-4-HO-1-Pyrd |
| 1-143 | MeO | F | cPr | 3-NMe₂-4-HO-1-Pyrd |
| 1-144 | MeO | F | cPr | 3-NH₂-4-MeO-1-Pyrd |
| 1-145 | MeO | F | cPr | 3-MeNH-4-MeO-1-Pyrd |
| 1-146 | MeO | F | cPr | 3-NMe₂-4-MeO-1-Pyrd |
| 1-147 | MeO | F | cPr | 3-(NMe₂.Me)-4-HO-1-Pyrd |
| 1-148 | MeO | F | cPr | 3-(NH₂Me)-4-MeO-1-Pyrd |
| 1-149 | MeO | F | cPr | 3-NH₂-4-EtO-1-Pyrd |
| 1-150 | MeO | F | cPr | 3-NH₂-4-PrO-1-Pyrd |
| 1-151 | MeO | F | cPr | 4-NH₂-1-Pip |
| 1-152 | MeO | F | cPr | 4-MeNH-1-Pip |
| 1-153 | MeO | F | cPr | 4-NMe₂-1-Pip |
| 1-154 | MeO | F | cPr | 4-NH₂-3-Me-1-Pip |
| 1-155 | MeO | F | cPr | 4-MeNH-3-Me-1-Pip |
| 1-156 | MeO | F | cPr | 4-(NH₂Me)-1-Pip |
| 1-157 | MeO | F | cPr | 4-(MeNHMe)-1-Pip |
| 1-158 | MeO | F | cPr | 4-(EtNHMe)-1-Pip |
| 1-159 | MeO | F | cPr | 3-NH₂-1-Hip |
| 1-160 | MeO | F | cPr | 3-NMe₂-1-Hip |

TABLE 1-continued

| CPd. No. | R¹ | X | R | D |
|---|---|---|---|---|
| 1-161 | MeO | Cl | cPr | 3-NH$_2$-1-Pyrd |
| 1-162 | MeO | Cl | cPr | 3-NH$_2$-4-Me-1-Pyrd |
| 1-163 | MeO | Cl | cPr | 3-(NH$_2$Me)-1-Pyrd |
| 1-164 | MeO | Cl | cPr | 3-NH$_2$-4-MeO-1-Pyrd |
| 1-165 | EtO | F | cPr | 3-NH$_2$-1-Azt |
| 1-166 | EtO | F | cPr | 3-NH$_2$-1-Pyrd |
| 1-167 | EtO | F | cPr | 3-(EtNHMe)-1-Pyrd |
| 1-168 | EtO | Cl | cPr | 3-NH$_2$-1-Pyrd |
| 1-169 | EtO | Cl | cPr | 3-NH$_2$-4-Me-1-Pyrd |
| 1-170 | EtO | Cl | cPr | 3-(NH$_2$Me)-1-Pyrd |
| 1-171 | MeO | F | Me | 3-NH$_2$-4-HO-1-Pyrd |
| 1-172 | MeO | F | Et | 3-NH$_2$-4-HO-1-Pyrd |
| 1-173 | MeO | F | Me | 3-NH$_2$-4-MeO-1-Pyrd |
| 1-174 | MeO | F | Et | 3-NH$_2$-4-MeO-1-Pyrd |
| 1-175 | MeO | F | Et | 3-NH$_2$-4-EtO-1-Pyrd |
| 1-176 | MeO | F | Et | 3-(MeNH)-4-MeO-1-Pyrd |
| 1-177 | MeO | F | Et | 3-BzNH-4-MeO-1-Pyrd |
| 1-178 | MeO | F | Et | 3-NMe$_2$-4-MeO-1-Pyrd |
| 1-179 | MeO | F | 2-FEt | 3-NH$_2$-4-HO-1-Pyrd |
| 1-180 | MeO | F | 2-FEt | 3-NH$_2$-4-MeO-1-Pyrd |
| 1-181 | MeO | F | 2-FEt | 3-NH$_2$-4-EtO-1-Pyrd |
| 1-182 | MeO | F | 2-FEt | 3-MeNH-4-MeO-1-Pyrd |
| 1-183 | MeO | F | 2-FEt | 3-BzNH-4-MeO-1-Pyrd |
| 1-184 | MeO | F | 2-FEt | 3-NMe$_2$-4-MeO-1-Pyrd |
| 1-185 | MeO | F | 2-FEt | 3-(NH$_2$Me)-4-MeO-1-Pyrd |
| 1-186 | MeO | F | MeNH— | 3-NH$_2$-4-HO-1-Pyrd |
| 1-187 | MeO | F | MeNH— | 3-NH$_2$-4-MeO-1-Pyrd |
| 1-188 | MeO | F | MeNH— | 3-NH$_2$-4-EtO-1-Pyrd |
| 1-189 | MeO | F | MeNH— | 3-NMe$_2$-4-MeO-1-Pyrd |
| 1-190 | MeO | F | cPr | 3-(NH$_2$Me)-3-HO-1-Pyrd |
| 1-191 | MeO | F | cPr | 3-(NH$_2$Me)-3-MeO-1-Pyrd |
| 1-192 | MeO | F | cPr | 3-(NH$_2$Me)-3-EtO-1-Pyrd |
| 1-193 | MeO | F | cPr | 3-(NH$_2$Me)-3-iPrO-1-Pyrd |
| 1-194 | MeO | F | 4-FPh | 3-NH$_2$-1-Azt |
| 1-195 | MeO | F | 4-FPh | 3-(NH$_2$Me)-1-Azt |
| 1-196 | MeO | F | 4-FPh | 3-NH$_2$-1-Pyrd |
| 1-197 | MeO | F | 4-FPh | 3-NH$_2$-4-Me-1-Pyrd |
| 1-198 | MeO | F | 4-FPh | 3-(NH$_2$Me)-1-Pyrd |
| 1-199 | MeO | F | 4-FPh | 3-(MeNHMe)-1-Pyrd |
| 1-200 | MeO | F | 4-FPh | 3-(NMe$_2$.Me)-1-Pyrd |
| 1-201 | MeO | F | 4-FPh | 3-(EtNHMe)-1-Pyrd |
| 1-202 | MeO | F | 4-FPh | 3-NH$_2$-4-HO-1-Pyrd |
| 1-203 | MeO | F | 4-FPh | 3-NH$_2$-4-MeO-1-Pyrd |
| 1-204 | MeO | F | 4-FPh | 3-BzNH-4-MeO-1-Pyrd |
| 1-205 | MeO | F | 4-FPh | 3-NH$_2$-4-EtO-1-Pyrd |
| 1-206 | MeO | F | 4-FPh | 4-NH$_2$-1-Pip |
| 1-207 | MeO | F | 2,4-diFPh | 3-NH$_2$-1-Azt |
| 1-208 | MeO | F | 2,4-diFPh | 3-(NH$_2$Me)-1-Azt |
| 1-209 | MeO | F | 2,4-diFPh | 3-NH$_2$-1-Pyrd |
| 1-210 | MeO | F | 2,4-diFPh | 3-NH$_2$-4-Me-1-Pyrd |
| 1-211 | MeO | F | 2,4-diFPh | 3-(NH$_2$Me)-1-Pyrd |
| 1-212 | MeO | F | 2,4-diFPh | 3-(MeNHMe)-1-Pyrd |
| 1-213 | MeO | F | 2,4-diFPh | 3-(NMe$_2$.Me)-1-Pyrd |
| 1-214 | MeO | F | 2,4-diFPh | 3-(EtNHMe)-1-Pyrd |
| 1-215 | MeO | F | 2,4-diFPh | 3-NH$_2$-4-HO-1-Pyrd |
| 1-216 | MeO | F | 2,4-diFPh | 3-NH$_2$-4-MeO-1-Pyrd |
| 1-217 | MeO | F | 2,4-diFPh | 3-BzNH-4-MeO-1-Pyrd |
| 1-218 | MeO | F | 2,4-diFPh | 3-NH$_2$-4-EtO-1-Pyrd |
| 1-219 | MeO | F | 2,4-diFPh | 4-NH$_2$-1-Pip |
| 1-220 | MeO | F | 4-HOPh | 3-NH$_2$-1-Azt |
| 1-221 | MeO | F | 4-HOPh | 3-NH$_2$-1-Pyrd |
| 1-222 | MeO | F | 4-HOPh | 3-MeNH-1-Pyrd |
| 1-223 | MeO | F | 4-HOPh | 3-NMe$_2$-1-Pyrd |
| 1-224 | MeO | F | 4-HOPh | 3-NH$_2$-4-Me-1-Pyrd |
| 1-225 | MeO | F | 4-HOPh | 3-NH$_2$-4-MeO-1-Pyrd |
| 1-226 | MeO | F | 4-MeOPh | 3-NH$_2$-1-Azt |
| 1-227 | MeO | F | 4-MeOPh | 3-NH$_2$-1-Pyrd |
| 1-228 | MeO | F | 4-MeOPh | 3-MeNH-1-Pyrd |
| 1-229 | MeO | F | 4-MeOPh | 3-NMe$_2$-1-Pyrd |
| 1-230 | MeO | F | 4-MeOPh | 3-NH$_2$-4-Me-1-Pyrd |
| 1-231 | MeO | F | 4-MeOPh | 3-NH$_2$-4-MeO-1-Pyrd |
| 1-232 | MeO | F | cPr | 3-NH$_2$-3-Me-1-Pyrd |
| 1-233 | MeO | F | cPr | 3-MeNH-3-Me-1-Pyrd |
| 1-234 | MeO | F | cPr | 3-EtNH-3-Me-1-Pyrd |
| 1-235 | MeO | F | cPr | 3-NMe$_2$-3-Me-1-Pyrd |
| 1-236 | MeO | F | cPr | 3-(NH$_2$Me)-4-Me-1-Pyrd |
| 1-237 | MeO | F | cPr | 3-(MeNHMe)-4-Me-1-Pyrd |
| 1-238 | MeO | F | cPr | 3-(EtNHMe)-4-Me-1-Pyrd |
| 1-239 | MeO | F | cPr | 3-(NMe$_2$.Me)-4-Me-1-Pyrd |
| 1-240 | MeO | F | cPr | 3-(MeNHMe)-3-MeO-1-Pyrd |
| 1-241 | MeO | F | cPr | 3-(EtNHMe)-3-MeO-1-Pyrd |
| 1-242 | MeO | F | cPr | 3-(NMe$_2$.Me)-3-MeO-1-Pyrd |
| 1-243 | MeO | F | Et | 3-(NH$_2$Me)-4-MeO-1-Pyrd |
| 1-244 | MeO | F | Et | 3-(EtNHMe)-4-MeO-1-Pyrd |
| 1-245 | MeO | F | 2-FEt | 3-(MeNHMe)-4-MeO-1-Pyrd |
| 1-246 | MeO | F | 2-FEt | 3-(EtNHMe)-4-MeO-1-Pyrd |
| 1-247 | MeO | F | cPr | 3-(NH$_2$Me)-4-HO-1-Pyrd |
| 1-248 | MeO | F | cPr | 3-(MeNHMe)-4-HO-1-Pyrd |
| 1-249 | MeO | F | cPr | 3-(EtNHMe)-4-HO-1-Pyrd |
| 1-250 | MeO | F | cPr | 3-(MeNHMe)-4-MeO 1-Pyrd |
| 1-251 | MeO | F | cPr | 3-(EtNHMe)-4-MeO-1-Pyrd |
| 1-252 | MeO | F | cPr | 3-(NMe$_2$.Me)-4-MeO-1-Pyrd |
| 1-253 | MeO | F | 4-FPh | 3-NH$_2$-3-Me-1-Pyrd |
| 1-254 | MeO | F | 4-FPh | 3-MeNH-3-Me-1-Pyrd |
| 1-255 | MeO | F | 4-FPh | 3-EtNH-3-Me-1-Pyrd |
| 1-256 | MeO | F | 4-FPh | 3-NMe$_2$-3-Me-1-Pyrd |
| 1-257 | MeO | F | 4-FPh | 3-(NH$_2$Me)-4-Me-1-Pyrd |
| 1-258 | MeO | F | 4-FPh | 3-(MeNHMe)-4-Me-1-Pyrd |
| 1-259 | MeO | F | 4-FPh | 3-(EtNHMe)-4-Me-1-Pyrd |
| 1-260 | MeO | F | 4-FPh | 3-(NMe$_2$.Me)-4-Me-1-Pyrd |
| 1-261 | MeO | F | 4-FPh | 3-(NH$_2$Me)-3-MeO-1-Pyrd |
| 1-262 | MeO | F | 4-FPh | 3-(MeNHMe)-3-MeO-1-Pyrd |
| 1-263 | MeO | F | 4-FPh | 3-(EtNHMe)-3-MeO-1-Pyrd |
| 1-264 | MeO | F | 4-FPh | 3-(NMe$_2$.Me)-3-MeO-1-Pyrd |
| 1-265 | MeO | F | 4-FPh | 3-(NH$_2$Me)-4-HO-1-Pyrd |
| 1-266 | MeO | F | 4-FPh | 3-(MeNHMe)-4-HO-1-Pyrd |
| 1-267 | MeO | F | 4-FPh | 3-(EtNHMe)-4-HO-1-Pyrd |
| 1-268 | MeO | F | 4-FPh | 3-(NH$_2$Me)-4-MeO-1-Pyrd |
| 1-269 | MeO | F | 4-FPh | 3-(MeNHMe)-4-MeO-1-Pyrd |
| 1-270 | MeO | F | 4-FPh | 3-(EtNHMe)-4-MeO-1-Pyrd |
| 1-271 | MeO | F | 4-FPh | 3-(NMe$_2$.Me)-4-MeO-1-Pyrd |
| 1-272 | MeO | F | 2,4-diFPh | 3-NH$_2$-3-Me-1-Pyrd |
| 1-273 | MeO | F | 2,4-diFPh | 3-MeNH-3-Me-1-Pyrd |
| 1-274 | MeO | F | 2,4-diFPh | 3-EtNH-3-Me-1-Pyrd |
| 1-275 | MeO | F | 2,4-diFPh | 3-NMe$_2$-3-Me-1-Pyrd |
| 1-276 | MeO | F | 2,4-diFPh | 3-(NH$_2$Me)-4-Me-1-Pyrd |
| 1-277 | MeO | F | 2,4-diFPh | 3-(MeNHMe)-4-Me-1-Pyrd |
| 1-278 | MeO | F | 2,4-diFPh | 3-(EtNHMe)-4-Me-1-Pyrd |
| 1-279 | MeO | F | 2,4-diFPh | 3-(NMe$_2$.Me)-4-Me-1-Pyrd |
| 1-280 | MeO | F | 2,4-diFPh | 3-(NH$_2$Me)-3-MeO-1-Pyrd |
| 1-281 | MeO | F | 2,4-diFPh | 3-(MeNHMe)-3-MeO-1-Pyrd |
| 1-282 | MeO | F | 2,4-diFPh | 3-(EtNHMe)-3-MeO-1-Pyrd |
| 1-283 | MeO | F | 2,4-diFPh | 3-(NMe$_2$.Me)-3-MeO-1-Pyrd |
| 1-284 | MeO | F | 2,4-diFPh | 3-(NH$_2$Me)-4-HO-1-Pyrd |
| 1-285 | MeO | F | 2,4-diFPh | 3-(MeNHMe)-4-HO-1-Pyrd |
| 1-286 | MeO | F | 2,4-diFPh | 3-(EtNHMe)-4-HO-1-Pyrd |
| 1-287 | MeO | F | 2,4-diFPh | 3-(NH$_2$Me)-4-MeO-1-Pyrd |
| 1-288 | MeO | F | 2,4-diFPh | 3-(MeNHMe)-4-MeO-1-Pyrd |
| 1-289 | MeO | F | 2,4-diFPh | 3-(EtNHMe)-4-MeO-1-Pyrd |
| 1-290 | MeO | F | 2,4-diFPh | 3-(NMe$_2$.Me)-4-MeO-1-Pyrd |
| 1-291 | MeO | F | cPr | 3-BzNH-4-MeO-1-Pyrd |
| 1-292 | MeO | F | cPr | 3-BzNH-4-EtO-1-Pyrd |

TABLE 2

| CPd. No. | R¹ | X | R | R⁸ | R⁹ |
|---|---|---|---|---|---|
| 2-1 | MeO | F | cPr | H | H |
| 2-2 | MeO | F | cPr | H | Me |
| 2-3 | MeO | F | cPr | Me | Me |
| 2-4 | MeO | Cl | cPr | H | Et |
| 2-5 | MeO | Cl | cPr | H | Pr |
| 2-6 | MeO | F | Me | H | Me |
| 2-7 | MeO | F | Et | H | Me |
| 2-8 | MeO | F | Et | Me | Me |
| 2-9 | MeO | F | 2-FEt | H | Me |
| 2-10 | MeO | F | 2-FEt | H | Et |
| 2-11 | MeO | F | 2-FEt | Me | Me |
| 2-12 | MeO | F | MeNH— | Me | Et |
| 2-13 | MeO | F | 4-FPh | H | H |
| 2-14 | MeO | F | 4-FPh | H | Me |
| 2-15 | MeO | F | 4-FPh | Me | Me |
| 2-16 | MeO | F | 2,4-diFPh | H | H |
| 2-17 | MeO | F | 2,4-diFPh | H | Me |
| 2-18 | MeO | F | 2,4-diFPh | Me | Me |
| 2-19 | MeO | F | 4-HOPh | Me | Me |
| 2-20 | MeO | F | 4-MeOPh | H | Me |

TABLE 3

| CPd. No. | R¹ | X | R | R⁷ |
|---|---|---|---|---|
| 3-1 | MeO | F | cPr | H |
| 3-2 | MeO | F | cPr | Me |
| 3-3 | MeO | Cl | cPr | H |
| 3-4 | MeO | F | Et | H |
| 3-5 | MeO | F | 2-FEt | H |
| 3-6 | MeO | F | MeNH— | H |
| 3-7 | MeO | F | 4-FPh | H |
| 3-8 | MeO | F | 4-FPh | Me |
| 3-9 | MeO | F | 2,4-diFPh | H |
| 3-10 | MeO | F | 2,4-diFPh | Me |
| 3-11 | MeO | F | 4-HOPh | H |
| 3-12 | MeO | F | 4-HOPh | Me |

TABLE 4

| CPd. No. | X | R | D |
|---|---|---|---|
| 4-1 | F | cPr | Mor |
| 4-2 | F | cPr | Thz |
| 4-3 | Cl | cPr | Mor |
| 4-4 | F | 4-FPh | Mor |
| 4-5 | F | 4-FPh | Thz |
| 4-6 | F | 2,4-diFPh | Mor |
| 4-7 | F | 2,4-diFPh | Thz |
| 4-8 | F | 4-HOPh | Mor |
| 4-9 | F | 4-HOPh | Thz |
| 4-10 | F | Me | 1-Piz |
| 4-11 | F | Me | 4-Me-1-Piz |
| 4-12 | F | Me | 3-Me-1-Piz |
| 4-13 | F | Me | 2,5-diMe-1-Piz |
| 4-14 | F | Me | 3,5-diMe-1-Piz |
| 4-15 | F | Me | 1-Hip |
| 4-16 | F | Me | 4-Me-1-Hip |
| 4-17 | F | Et | 1-Piz |
| 4-18 | F | Et | 4-Me-1-Piz |
| 4-19 | F | Et | 3-Me-1-Piz |
| 4-20 | F | Et | 3,4-diMe-1-Piz |
| 4-21 | F | Et | 2,4,5-triMe-1-Piz |
| 4-22 | F | Et | 3,4,5-triMe-1-Piz |
| 4-23 | F | Et | 1-Hip |
| 4-24 | F | Et | 4-Me-1-Hip |
| 4-25 | F | 2-FEt | 1-Piz |
| 4-26 | F | 2-FEt | 4-Me-1-Piz |
| 4-27 | F | 2-FEt | 3-Me-1-Piz |
| 4-28 | F | 2-FEt | 3,4-diMe-1-Piz |
| 4-29 | F | 2-FEt | 2,5-diMe-1-Piz |
| 4-30 | F | 2-FEt | 2,4,5-triMe-1-Piz |
| 4-31 | F | 2-FEt | 3,5-diMe-1-Piz |
| 4-32 | F | 2-FEt | 3,4,5-triMe-1-Piz |
| 4-33 | F | 2-FEt | 1-Hip |
| 4-34 | F | 2-FEt | 4-Me-1-Hip |
| 4-35 | F | Pr | 4-Me-1-Piz |
| 4-36 | F | iPr | 1-Piz |
| 4-37 | F | MeNH— | 1-Piz |
| 4-38 | F | MeNH— | 4-Me-1-Piz |
| 4-39 | F | MeNH— | 3-Me-1-Piz |
| 4-40 | F | MeNH— | 1-Hip |
| 4-41 | F | MeNH— | 4-Me-1-Hip |
| 4-42 | F | Me | 3-NH₂-1-Pyrd |
| 4-43 | F | Me | 3-NH₂-4-Me-1-Pyrd |
| 4-44 | F | Me | 3-MeNH-1-Pyrd |
| 4-45 | F | Me | 3-EtNH-1-Pyrd |
| 4-46 | F | Me | 3-NMe₂-4-Me-1-Pyrd |
| 4-47 | F | Me | 3-(NH₂Me)-1-Pyrd |
| 4-48 | F | Me | 3-(MeNH₂Me)-1-Pyrd |
| 4-49 | F | Me | 3-(EtNH₂Me)-1-Pyrd |
| 4-50 | F | Me | 3-(NMe₂.Me)-1-Pyrd |
| 4-51 | F | Et | 3-NH₂-1-Pyrd |
| 4-52 | F | Et | 3-NH₂-4-Me-1-Pyrd |
| 4-53 | F | Et | 4-NH₂-2-Me-1-Pyrd |
| 4-54 | F | Et | 3-MeNH-1-Pyrd |
| 4-55 | F | Et | 3-MeNH-4-Me-1-Pyrd |
| 4-56 | F | Et | 4-MeNH-2-Me-1-Pyrd |
| 4-57 | F | Et | 3-NMe₂-1-Pyrd |
| 4-58 | F | Et | 3-NMe₂-4-Me-1-Pyrd |
| 4-59 | F | Et | 4-NMe₂-2-Me-1-Pyrd |
| 4-60 | F | Et | 3-N(Me)(Et)-1-Pyrd |
| 4-61 | F | Et | 3-(NH₂Me)-1-Pyrd |
| 4-62 | F | Et | 3-(MeNHMe)-1-Pyrd |
| 4-63 | F | Et | 3-(EtNHMe)-1-Pyrd |
| 4-64 | F | Et | 3-(NMe₂.Me)-1-Pyrd |
| 4-65 | F | 2-FEt | 3-NH₂-1-Pyrd |
| 4-66 | F | 2-FEt | 3-NH₂-4-Me-1-Pyrd |
| 4-67 | F | 2-FEt | 4-NH₂-2-Me-1-Pyrd |
| 4-68 | F | 2-FEt | 3-MeNH-1-Pyrd |
| 4-69 | F | 2-FEt | 3-MeNH-4-Me-1-Pyrd |
| 4-70 | F | 2-FEt | 3-EtNH-1-Pyrd |
| 4-71 | F | 2-FEt | 3-NMe₂-1-Pyrd |
| 4-72 | F | 2-FEt | 3-NMe₂-4-Me-1-Pyrd |
| 4-73 | F | 2-FEt | 4-NMe₂-2-Me-1-Pyrd |
| 4-74 | F | 2-FEt | 3-N(Me)(Et)-1-Pyrd |
| 4-75 | F | 2-FEt | 3-(NH₂Me)-1-Pyrd |
| 4-76 | F | 2-FEt | 3-(MeNHMe)-1-Pyrd |
| 4-77 | F | 2-FEt | 3-(EtNHMe)-1-Pyrd |
| 4-78 | F | 2-FEt | 3-(NMe₂.Me)-1-Pyrd |
| 4-79 | F | MeNH— | 3-NH₂-1-Pyrd |
| 4-80 | F | MeNH— | 3-NH₂-4-Me-1-Pyrd |
| 4-81 | F | MeNH— | 3-MeNH-1-Pyrd |
| 4-82 | F | MeNH— | 3-NMe₂-1-Pyrd |
| 4-83 | F | MeNH— | 3-EtNH-1-Pyrd |
| 4-84 | F | Me | 3-MeNH-3-Me-1-Pyrd |
| 4-85 | F | Me | 3-(EtNHMe)-4-Me-1-Pyrd |
| 4-86 | F | Et | 3-NH₂-3-Me-1-Pyrd |
| 4-87 | F | Et | 3-(NH₂Me)-4-Me-1-Pyrd |
| 4-88 | F | 2-FEt | 3-NH₂-3-Me-1-Pyrd |
| 4-89 | F | 2-FEt | 3-(NH₂Me)-4-Me-1-Pyrd |
| 4-90 | F | 2-FEt | 3-(EtNHMe)-4-Me-1-Pyrd |

Of the compounds listed above, the following compounds are preferred: Compounds Nos. 1-1, 1-2, 1-3, 1-6, 1-7, 1-11, 1-17, 1-23, 1-24, 1-25, 1-63, 1-80, 1-82, 1-116, 1-125, 1-130, 1-137, 1-139, 1-140, 1-141, 1-144, 1-148, 1-149, 1-191, 1-232, 1-236, 1-238, 1-241, 1-247, 1-249, 1-251, 3-1, 4-1 and 4-2.

In particular, in view of their excellent activity, the following compounds are most preferred:

1-1. 1-Cyclopropyl-6-fluoro-8-methoxy-7-(1-piperazinyl)-1,4-dihydro-4-oxoquinoline-3-carboxylic acid 1-2. 1-Cyclopropyl-6-fluoro-8-methoxy-7-(3-methyl-1-piperazinyl)-1,4-dihydro-4-oxoquinoline-3-carboxylic acid 1-6. 1-Cyclopropyl-6-fluoro-8-methoxy-7-(4-methyl-1-piperazinyl)-1,4-dihydro-4-oxoquinoline-3-carboxylic acid 1-7. 1-Cyclopropyl-6-fluoro-8-methoxy-7-(3,4-dimethyl-1-piperazinyl)-1,4-dihydro-4-oxoquinoline-3-carboxylic acid 1-11. 1-Cyclopropyl-6-fluoro-8-methoxy-7-[4-(2-hydroxyethyl)-1-piperazinyl]-1,4-dihydro-4-oxoquinoline-3-carboxylic acid 1-23. 1-Cyclopropyl-6-fluoro-8-methoxy-7-(1-homopiperazinyl)-1,4-dihydro-4-oxoquinoline-3-carboxylic acid 1-63. 1-(2,4-Difluorophenyl)-6-fluoro-8-methoxy-7-(1-piperazinyl)-1,4-dihydro-4-oxoquinoline-3-carboxylic acid 1-80. 1-Cyclopropyl-6-fluoro-8-methoxy-7-(3-hydroxy-1-pyrrolidinyl)-1,4-dihydro-4-oxoquinoline-3-carboxylic acid 1-125. 1-Cyclopropyl-6-fluoro-8-methoxy-7-(3-amino-1-pyrrolidinyl)-1,4-dihydro-4-oxoquinoline-3-carboxylic acid 1-130. 1-Cyclopropyl-6-fluoro-8-methoxy-7-(3-amino-4-methyl-1-pyrrolidinyl)-1,4-dihydro-4-oxoquinoline-3-carboxylic acid 1-137. 1-Cyclopropyl-6-fluoro-8-methoxy-7-[3-(aminomethyl)-1-pyrrolidinyl]-1,4-dihydro-4-oxoquinoline-3-carboxylic acid 1-139. 1-Cyclopropyl-6-fluoro-8-methoxy-7-[3-(ethylamino)methyl)-1-pyrrolidinyl]-1,4-dihydro-4-oxoquinoline-3-carboxylic acid 1-144. 1-Cyclopropyl-6-fluoro-8-methoxy-7-(3-amino-4-methoxy-1-pyrrolidinyl)-1,4-dihydro-4-oxoquinoline-3-carboxylic acid In the case of Compounds Nos. 1-130 and 1-144, both the cis and trans isomers (isomerism with respect to substituents on the pyrrolidine ring) are preferred.

Also preferred are pharmaceutically acceptable salts, esters and amides, more preferably salts and esters, and most preferably hydrochlorides, of the above preferred and most preferred Compounds.

In general terms, the compounds of the present invention may be prepared by reacting a compound of formula (II):

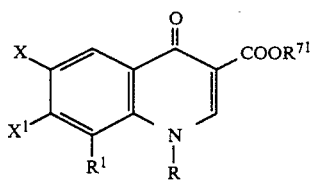

(in which R, $R^1$ and X are as defined above; X' represents a halogen atom and may be the same as or different from the halogen atom represented by X, preferably the same; and $R^{7'}$ represents a hydrogen atom or a carboxy-protecting group) or an active derivative or equivalent thereof with a compound of formula (III):

Y—H        (III)

(in which Y is as defined above) or an active derivative or equivalent thereof, and, if necessary, subjecting the product to any one or more of the reactions: deprotection, salification, esterification and amidation.

$R^{7'}$ may represent any carboxy-protecting group known in organic chemistry for use with this type of compound and may be incorporated into and (if desired) removed from the compound by well known methods which require no elaboration here. However, $R^{7'}$ is preferably a hydrogen atom or a $C_1$-$C_6$, preferably $C_1$-$C_4$, alkyl group, for example a methyl, ethyl, propyl, isopropyl, butyl, t-butyl, or hexyl group, most preferably a hydrogen atom, a methyl group or an ethyl group.

Alternatively, $R^{7'}$ may represent a boron difluoride ($BF_2$) group. In this case, the boron difluoride group will normally form a covalent linkage with the oxygen atom at the 4-position of the quinoline ring and the compound of formula (II) (because of the method of its preparation) will normally be a hydrogen A preferred method of preparing the compounds of the invention is illustrated in more detail by reaction scheme A:

Reaction Scheme A:

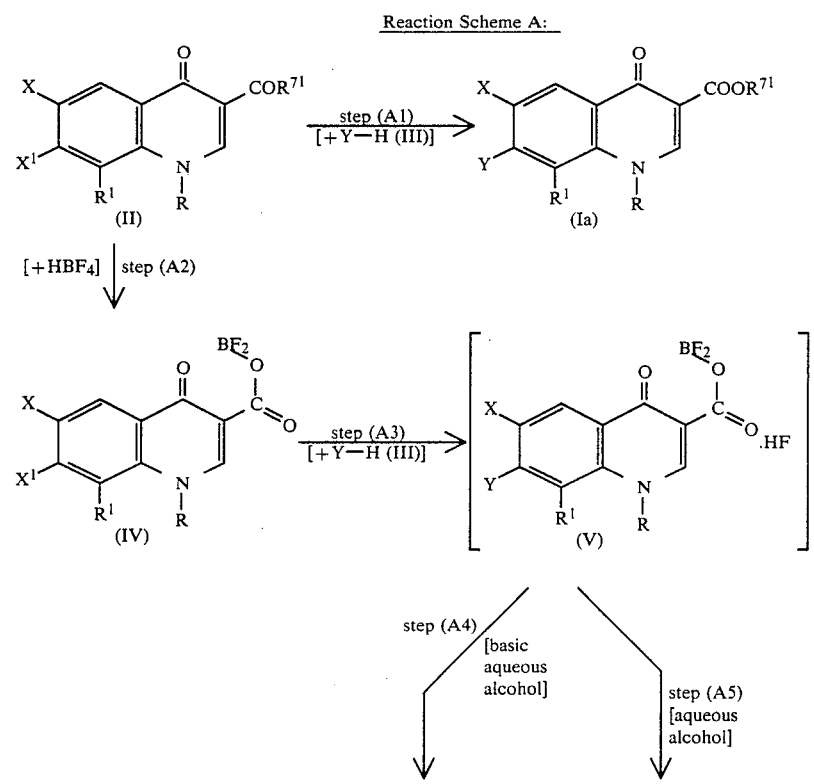

-continued

Reaction Scheme A:

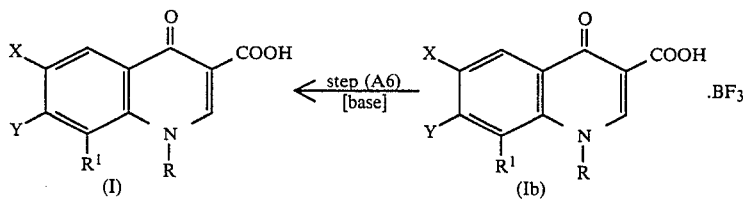

In the above formulae, R, $R^1$, $R^{7'}$, X' and Y are as defined above. X' represents a halogen atom and may be the same as or different from the halogen atom represented by X; it is preferably a fluorine atom.

In the above reactions, the compounds of formula (I) of the present invention can be prepared by reacting a compound (II) or its boron difluoride chelate (IV) with an amine compound of formula (III). The reaction may be effected in the presence or absence of an acid binding agent and in the presence or absence of a solvent.

The molar ratio of the compound of formula (II) to the amine of formula (III) is not critical, although we generally prefer to employ equimolar amounts of the two reagents or a molar excess of the amine.

Where a solvent is employed, its nature is not particularly critical, provided that it has no adverse effect on the reaction. Examples of suitable solvents include: aprotic polar solvents, such as dimethyl sulfoxide, dimethylformamide, hexamethylphosphoric triamide or dimethylacetamide; ketones, such as acetone or methyl ethyl ketone; ethers, such as diethyl ether, tetrahydrofuran or dioxane; esters, such as ethyl acetate; alcohols, such as methanol, ethanol, propanol, isopropanol or butanol; and nitriles, such as acetonitrile. Of these, the aprotic polar solvents are preferred.

Where an acid binding agent is employed, its nature is not particularly critical, provided that it has no adverse effect on the reaction and that it is capable of binding to, and hence effectively removing from the reaction mixture, the acid produced in the course of the reaction. Examples of suitable acid binding agents include: tertiary amines, such as triethylamine, tributylamine, pyridine, picoline, lutidine or collidine; and inorganic bases, preferably alkali metal carbonates, such as sodium carbonate or potassium carbonate. The amount of acid binding agent employed is preferably equimolar or a molar excess, with respect to to the compound of formula (II), more preferably a molar ratio of said compound of formula (II) to said acid binding agent of from 1:1 to 1:5. However, where one of the afore-mentioned amines is used as acid binding agent, it is preferably employed in a large excess, in which case it may serve both as the acid binding agent and as solvent. The reaction may also proceed smoothly even when an acid binding agent is not employed because an excess of the amine (III) can serve as the acid binding agent.

The reaction may be carried out over a wide range of temperatures, and the exact reaction temperature is not critical to the invention. However, we generally find it convenient to carry out the reaction at a temperature ranging from room temperature to 200° C.

After the reaction is complete, the desired compound of the invention can be recovered from the reaction mixture by treatment in a conventional manner, and, if desired, may be further purified by such conventional techniques as recrystallization or the various chromatography techniques, notably column chromatography.

In the reactions represented by steps A2 to A6, a chelate (V) of the desired compound is obtained first, and this is then converted into the $BF_3$ addition product of compound of formula (I) or the compound of formula (I) itself by treatment with an aqueous alcohol or a basic aqueous alcohol. The $BF_3$ addition product of the compound of formula (I) is easily converted into the compound (I) itself by treatment with a base.

Examples of bases which may be employed include: alkali metal hydroxides, such as sodium hydroxide or potassium hydroxide; alkali metal carbonates, such as sodium carbonate or potassium carbonate; and tertiary amines, such as triethylamine or 4-dimethylaminopyridine.

The compound of formula (I) or its $BF_3$ addition product may, if desired, be converted into a desired salt by conventional means.

Conversion of the compound of formula (II) to the boron fluoride chelate (IV) can be carried out, for example, by reaction with hydrofluoroboric acid by the method described in Japanese Patent Application Kokai (i.e. as laid open to public inspection) No. 67290/84.

The compound of formula (I) thus prepared may exist as a mixture of optical isomers due to the presence of an asymmetric carbon atom in the moiety of the compound represented by Y or as geometric (cis or trans) isomers due to, for example, the presence of two or more substituents on the heterocyclic group represented by Y. In such a case, individual isomers of the compound may be prepared, if desired, by using as the starting material YH (III) a compound which has been optically resolved or separated in advance to obtain the corresponding optical or geometric isomer of the desired compound (I). Alternatively, a mixture of optical or geometric isomers of the compound (I) may be prepared, and these may be resolved or separated into the individual isomers by conventional techniques.

The compounds of formula (II) used as starting materials in the afore-mentioned reactions are novel compounds and can be prepared, for instance, by the following reaction schemes, e.g. as described in Japanese Patent Applications Kokai No. 74667/83 and No. 72885/85, for Reaction Scheme E.

Reaction Scheme B:

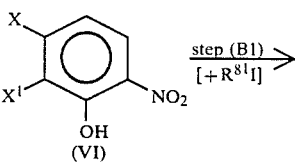

-continued
Reaction Scheme B:
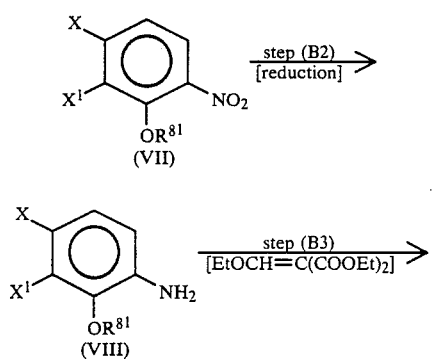
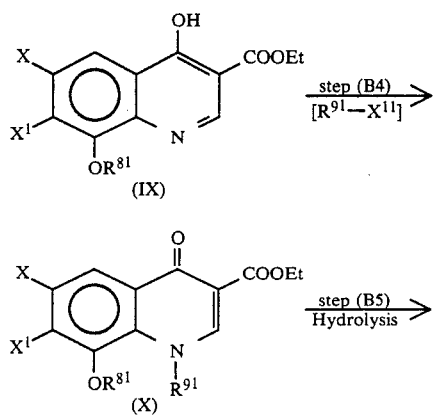
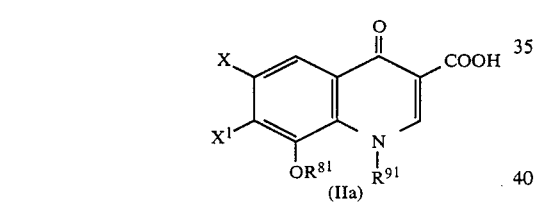
Reaction Scheme C:
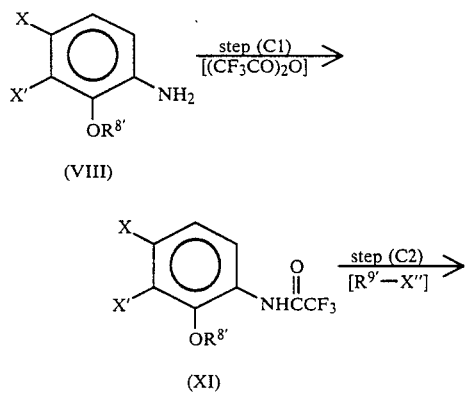
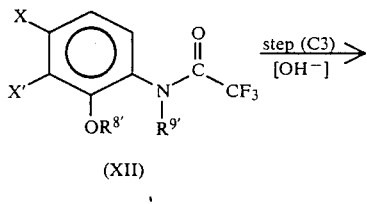
-continued
Reaction Scheme C:
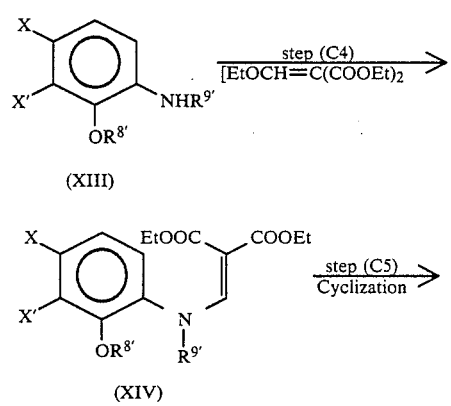
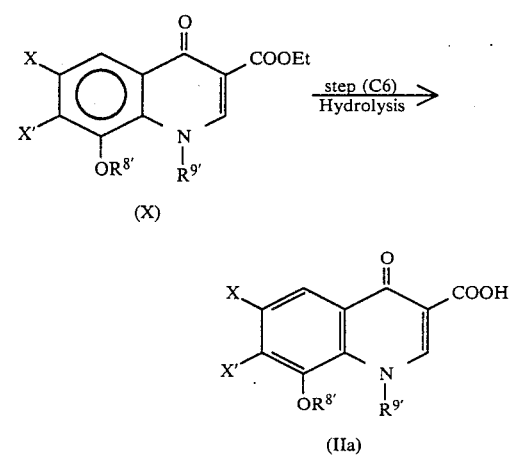
Reaction Scheme D:
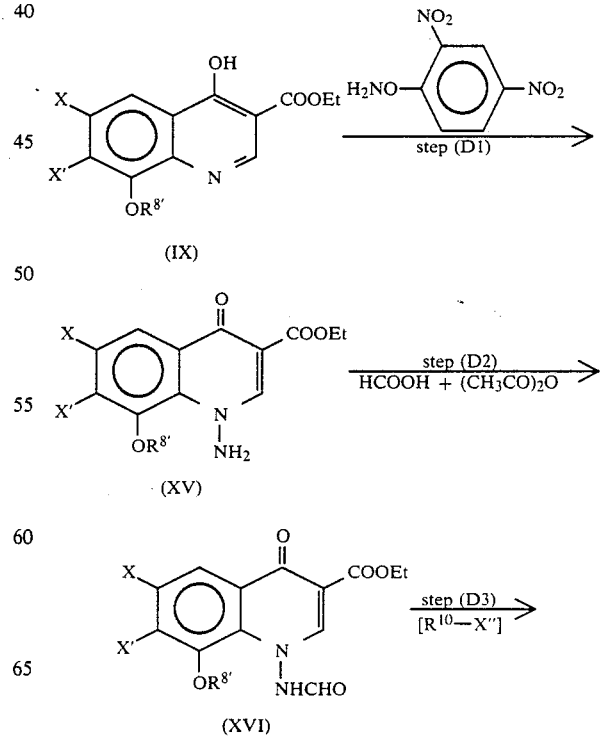

-continued
Reaction Scheme D:

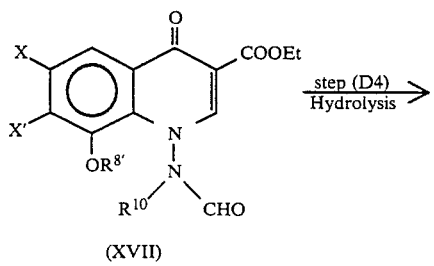

(XVII)

$\xrightarrow{\text{step (D4)}}_{\text{Hydrolysis}}$

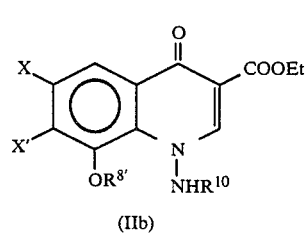

(IIb)

Reaction Scheme E:

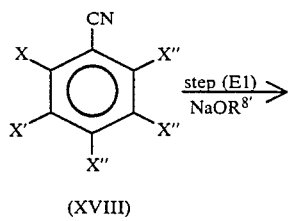

(XVIII)

$\xrightarrow{\text{step (E1)}}_{\text{NaOR}^{8'}}$

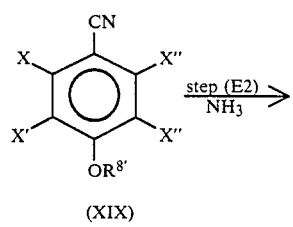

(XIX)

$\xrightarrow{\text{step (E2)}}_{\text{NH}_3}$

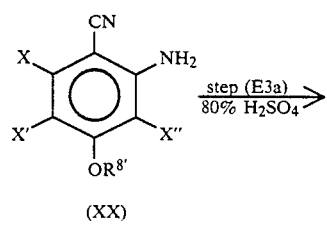

(XX)

$\xrightarrow{\text{step (E3a)}}_{80\%\ \text{H}_2\text{SO}_4}$

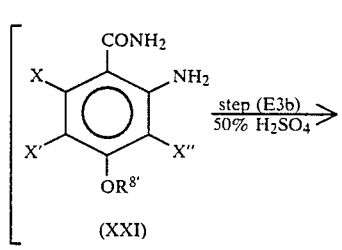

(XXI)

$\xrightarrow{\text{step (E3b)}}_{50\%\ \text{H}_2\text{SO}_4}$

-continued
Reaction Scheme E:

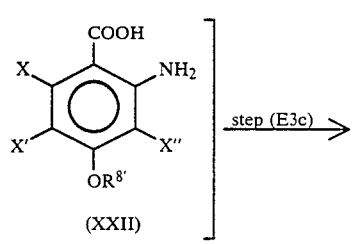

(XXII)

$\xrightarrow{\text{step (E3c)}}$

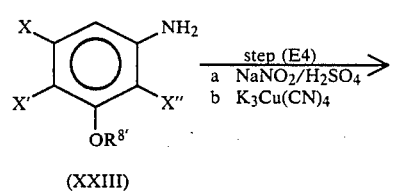

(XXIII)

$\xrightarrow[\text{b } \text{K}_3\text{Cu(CN)}_4]{\text{step (E4)}\atop\text{a  NaNO}_2/\text{H}_2\text{SO}_4}$

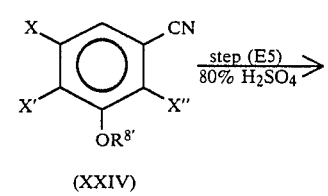

(XXIV)

$\xrightarrow{\text{step (E5)}}_{80\%\ \text{H}_2\text{SO}_4}$

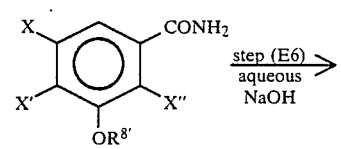

(XXV)

$\xrightarrow{\text{step (E6)}}_{\text{aqueous NaOH}}$

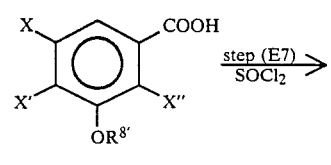

(XXVI)

$\xrightarrow{\text{step (E7)}}_{\text{SOCl}_2}$

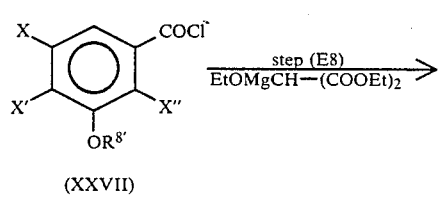

(XXVII)

$\xrightarrow{\text{step (E8)}}_{\text{EtOMgCH—(COOEt)}_2}$

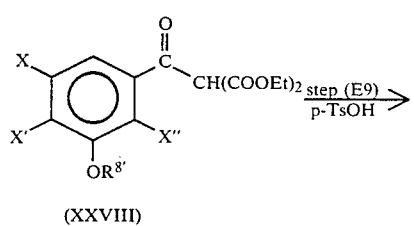

(XXVIII)

$\xrightarrow{\text{step (E9)}}_{p\text{-TsOH}}$

-continued
Reaction Scheme E:

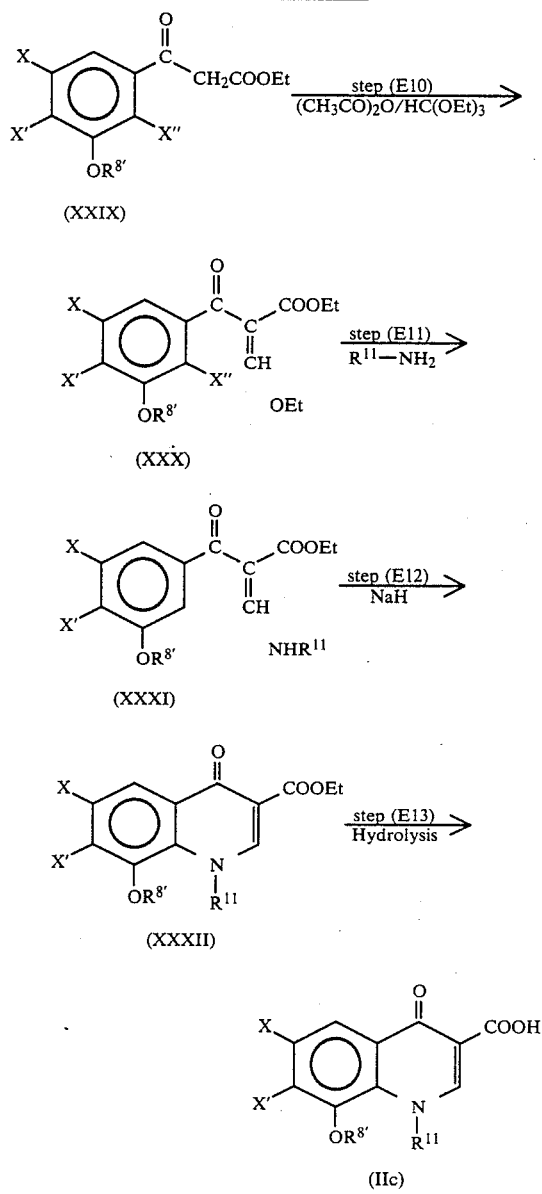

Reaction Scheme F:

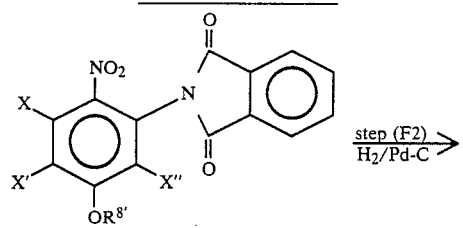

Reaction Scheme F:

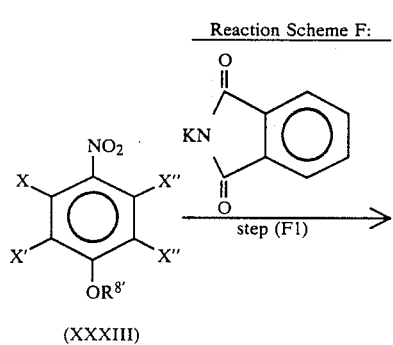

In the above formulae, $R^{8'}$ represents an alkyl group containing from 1 to 3 carbon atoms corresponding to the alkoxy group represented by $R^1$. $R^{9'}$ represents a $C_1$–$C_3$ alkyl or haloalkyl group corresponding to R. $R^{10}$ represents a $C_1$–$C_3$ alkyl group corresponding to R. $R^{11}$ represents a $C_1$–$C_3$ alkyl or haloalkyl group, an optionally substituted phenyl group or a cycloalkyl group corresponding to R. $R^{12}$ represents a $C_1$–$C_5$ alkyl group. X" represents a halogen atom, which may be the same as or different from the halogen atom(s) represented by X and X'; in reaction scheme E, X" preferably represents a fluorine atom. Et represents the ethyl group. Ts represents the tosyl (toluenesulfonyl) group.

The reaction conditions and treatment after completion of the reaction in each Step are described in more detail in the following Preparations. Of course, the details of reaction conditions etc given in these Preparations are merely by way of example and it will be appreciated that these well known reactions may be conducted in a variety of different ways.

The compounds of the invention possess a powerful antibacterial activity. Estimation by the agar plate dilution method showed an excellent growth inhibitory effect against a wide range of pathogenic bacteria, including Gram-positive bacteria such as *Staphylococcus aureus* or Enterococcus species, and Gram-negative bacteria such as *Escherichia coli*, Shigella, *Klebsiella pneumoniae*, Morganella, Serratia, Enterobacter, Salmonella or *Pseudomonas aeruginosa*, including normally resistant strains thereof.

The compounds of the invention can be administered as conventional pharmaceutical formulations, depending upon the intended route of administration. For example, for oral administration, they may be formulated as powders, granules, tablets, capsules, syrups or similar orally administerable formulations, which can be produced by mixing the active compound with carriers, excipients or diluting agents, such as glucose, sucrose, lactose, sorbitol, starch, polyvinylpyrrolidone, mannitol, calcium carbonate, calcium phosphate, sodium chloride or boric acid. For parenteral administration, they may be formulated as conventional injections suitable for, for example, intravenous or intramuscular injection. The dose will vary, depending upon the nature of the disorder, the route of administration, and the symptoms, age and body weight of the patient; however, for an adult human patient, a suitable dose for oral administration would be from 100 mg to 1000 mg per day, which could be given in a single dose or in divided doses.

The invention is further illustrated by the following Examples, which illustrate the preparation of various of the compounds of the invention. The preparation of certain of the starting materials employed in these Examples is illustrated in the subsequent Preparations. The activity of certain of the compounds of the invention is illustrated by the subsequent Biological Activity data.

EXAMPLE 1

1-Cyclopropyl-6-fluoro-8-methoxy-7-(1-piperazinyl)-1,4-dihydro-4-oxoquinoline-3-carboxylic acid hydrochloride

[Steps (A3)+(A4)]

(a) 0.11 g (0.00032 mole) of 1-cyclopropyl-6,7-difluoro-8-methoxy-1,4-dihydro-4-oxoquinoline-3-carboxylic acid boron difluoride chelate (IV) (prepared as described in Preparation 7) was dissolved in 0.5 ml of dimethyl sulfoxide, and 0.11 g (0.0012 mole) of anhydrous piperazine was added to the resulting solution. The mixture was then allowed to stand at room temperature overnight, after which it was poured into 50 ml of diethyl ether. The yellow crystals which precipitated were collected by filtration and dissolved in 30 ml of 80% aqueous ethanol and 5 ml of triethylamine, and the resulting solution was heated under reflux for 4 hours. The reaction mixture was then filtered while hot to remove insoluble material, and the filtrate was concentrated by evaporation under reduced pressure to give a crystalline substance, which was washed with ethanol to afford 0.07 g of 1-cyclopropyl-6-fluoro-8-methoxy-7-(1-piperazinyl)-1,4-dihydro-4-oxoquinoline-3-carboxylic acid as colorless powdery crystals, melting at 177°–178° C.

(b) The whole of the crystals obtained as described in Step (a) above were suspended in 30 ml of ethanol, and 1 ml of concentrated hydrochloric acid was added to the resulting suspension. The mixture was then concentrated by evaporation under reduced pressure to give a residue, which was washed with ethanol to afford 0.06 g of the hydrochloride of the title compound as a colorless powder melting at 246°–248° C. (with decomposition).

Elemental analysis: Calculated for $C_{18}H_{20}FN_3O_4 \cdot HCl \cdot \frac{1}{2}H_2O$: C, 53.14%; H, 5.45%; N, 10.33%. Found: C, 53.31%; H, 5.47%; N, 10.36%.

EXAMPLE 2

1-Cyclopropyl-6-fluoro-8-methoxy-7-(4-methyl-1-piperazinyl)-1,4-dihydro-4-oxoquinoline-3-carboxylic acid hydrochloride

[Step (A1)]

0.12 g (0.0012 mole) of N-methylpiperazine was added to a solution of 0.09 g (0.0003 mole) of 1-cyclopropyl-6,7-difluoro-8-methoxy-1,4-dihydro-4-oxoquinoline-3-carboxylic acid (IIc) (prepared as described in Preparation 6) in 0.5 ml of dimethyl sulfoxide, and the mixture was stirred at 70° C. for 6 hours. At the end of this time, the solvent and the excess N-methylpiperazine were removed by evaporation under reduced pressure at the same temperature, and the residue was washed with ethyl acetate and subjected to silica gel column chromatography, eluted with methanol, to afford 0.03 g of 1-cyclopropyl-6-fluoro-8-methoxy-7-(4-methyl-1-piperazinyl)-1,4-dihydro-4-oxoquinoline-3-carboxylic acid as colorless powdery crystals, melting at 211°–214° C.

The whole of the free amine thus prepared was converted into 0.02 g of the hydrochloride, which was a colorless powder melting at 225°–228° C. (with decomposition), in the same manner as described in Example 1.

Elemental analysis: Calculated for $C_{19}H_{22}FN_3O_4 \cdot HCl \cdot H_2O$: C, 53.08%; H, 5.86%; N, 9.78%. Found: C, 53.12%; H, 5.54%; N, 9.68%.

EXAMPLE 3

1-Cyclopropyl-6-fluoro-8-methoxy-7-(3,4-dimethyl-1-piperazinyl)-1,4-dihydro-4-oxoquinoline-3-carboxylic acid hydrochloride A solution of 1.5 g (0.004 mole) of 1-cyclopropyl-6-fluoro-8-methoxy-7-(3-methyl-1-piperazinyl)-1,4-dihydro-4-oxoquinoline-3-carboxylic acid (free form) (prepared as described in Example 22, but omitting the final reaction with hydrochloric acid) in a mixture of 75 ml of 90% aqueous formic acid and 45 ml of 37% aqueous formaldehyde was heated under reflux for 15 hours. 8 ml of concentrated hydrochloric acid were then added to the reaction mixture, and the solvent (formic acid, formalin and water) was then removed by evaporation under reduced pressure. Methanol was then added to the residue, and the resulting solution was filtered to remove insoluble material. The filtrate was evaporated to dryness under reduced pressure, and the residue was washed with ethanol to afford 1.35 g of 1-cyclopropyl-6-fluoro-8-methoxy-7-(3,4-dimethyl-1-piperazinyl)-1,4- dihydro-4-oxoquinoline-3-carboxylic acid hydrochloride as a colorless powder melting at 218°–221° C. (with decomposition).

Elemental analysis: Calculated for $C_{20}H_{24}FN_3O_4 \cdot HCl \cdot 3/2H_2O$: C, 53.03%; H, 6.23%; N, 9.28%. Found: C, 53.07%; H, 5.85%; N, 9.10%.

EXAMPLES 4 TO 21

The following compounds were also prepared according to the same procedures as described in the appropriate one of Example 1 and Example 2.

EXAMPLE 4

1-Cyclopropyl-6-fluoro-8-methoxy-7-(3-amino-1-pyrrolidinyl)-1,4-dihydro-4-oxoquinoline-3-carboxylic acid hydrate, melting at 199°–201° C.

EXAMPLE 5

1-Cyclopropyl-6-fluoro-8-methoxy-7-(3-aminomethyl-1-pyrrolidinyl)-1,4-dihydro-4-oxoquinoline-3-carboxylic acid hydrate, melting at 200°–205° C.

EXAMPLE 6

1-Cyclopropyl-6-fluoro-8-methoxy-7-(3-aminomethyl-1-azetidinyl)-1,4-dihydro-4-oxoquinoline-3-carboxylic acid hydrochloride hydrate, melting at 212°–215° C.

EXAMPLE 7

1-Cyclopropyl-6-fluoro-8-methoxy-7-(1-homopiperazinyl)-1,4-dihydro-4-oxoquinoline-3-carboxylic acid hemihydrate, melting at 208°–209° C.

EXAMPLE 8

1-Cyclopropyl-6-fluoro-8-methoxy-7-(4-methyl-1-homopiperazinyl)-1,4-dihydro-4-oxoquinoline-3-carboxylic acid hydrate, melting at 172°–175° C.

EXAMPLE 9

1-Cyclopropyl-6-fluoro-8-methoxy-7-(4-formyl-1-piperazinyl)-1,4-dihydro-4-oxoquinoline-3-carboxylic acid hydrate, melting at 205°–207° C.

EXAMPLE 10

1-Cyclopropyl-6-fluoro-8-methoxy-7-(3-oxo-1-piperazinyl)-1,4-dihydro-4-oxoquinoline-3-carboxylic acid hydrate, melting at 239°–241° C.

EXAMPLE 11

1-Cyclopropyl-6-fluoro-8-methoxy-7-(4-aminopiperidino)-1,4-dihydro-4-oxoquinoline-3-carboxylic acid hydrochloride hydrate, melting at 240°–250° C. (with decomposition).

EXAMPLE 12

1-Cyclopropyl-6-fluoro-8-methoxy-7-(4-dimethylaminopiperidino)-1,4-dihydro-4-oxoquinoline-3-carboxylic acid hydrochloride, melting at 220°–222° C.

EXAMPLE 13

1-Cyclopropyl-6-fluoro-8-methoxy-7-(3-dimethylaminomethyl-1-pyrrolidinyl)-1,4-dihydro-4-oxoquinoline-3-carboxylic acid sesquihydrate, melting at 202°–204° C.

EXAMPLE 14

1-Cyclopropyl-6-fluoro-8-methoxy-7-(3-amino-1-azetidinyl)-1,4-dihydro-4-oxoquinoline-3-carboxylic acid hydrate, melting at 228°–238° C. (with decomposition).

EXAMPLE 15

1-Cyclopropyl-6-fluoro-8-methoxy-7-(3-dimethylamino-1-azetidinyl)-1,4-dihydro-4-oxoquinoline-3-carboxylic acid hydrochloride hydrate, melting at 199°–203° C. (with decomposition).

EXAMPLE 16

1-Cyclopropyl-6-fluoro-8-methoxy-7-[4-(2-hydroxyethyl)-1-piperazinyl]-1,4-dihydro-4-oxoquinoline-3-carboxylic acid hydrate, melting at 204°–205° C.

EXAMPLE 17

1-Cyclopropyl-6-fluoro-8-methoxy-7-[4-(acetylmethyl)-1-piperazinyl]-1,4-dihydro-4-oxoquinoline-3-carboxylic acid hydrate, melting at 165°–168° C.

EXAMPLE 18

1-Cyclopropyl-6-fluoro-8-methoxy-7-[4-(carboxymethyl)-1-piperazinyl]-1,4-dihydro-4-oxoquinoline-3-carboxylic acid hemihydrate, melting at 238°–239° C. (with decomposition).

EXAMPLE 19

1-Cyclopropyl-6-fluoro-8-methoxy-7-(1-imidazolyl)-1,4-dihydro-4-oxoquinoline-3-carboxylic acid hydrochloride sesquihydrate, melting at 270°–280° C. (with decomposition).

EXAMPLE 20

1-Cyclopropyl-6-fluoro-8-methoxy-7-(3,5-dimethyl-1-piperazinyl)-1,4-dihydro-4-oxoquinoline-3-carboxylic acid hydrochloride hemihydrate, melting at 278°–280° C. (with decomposition).

EXAMPLE 21

1-Cyclopropyl-6-fluoro-8-methoxy-7-(3,4,5-trimethyl-1-piperazinyl)-1,4-dihydro-4-oxoquinoline-3-carboxylic acid hydrochloride dihydrate, melting at 234°–235° C. (with decomposition).

EXAMPLE 22

1-Cyclopropyl-6-fluoro-8-methoxy-7-(3-methyl-1-piperazinyl)-1,4-dihydro-4-oxoquinoline-3-carboxylic acid hydrochloride

[Step (A3)]

6.8 g (0.068 mole) of 2-methylpiperazine were added to a solution of 5.8 g (0.017 mole) of 1-cyclopropyl-6,7-difluoro-8-methoxy-1,4-dihydro-4-oxoquinoline-3-carboxylic acid boron difluoride chelate (IV) (prepared as described in Preparation 7) in 4 ml of dimethyl sulfoxide, and the mixture was allowed to stand at room temperature overnight. At the end of this time, the solvent and the excess 2-methylpiperazine were removed by evaporation under reduced pressure, and the residue was washed with diethyl ether to give the chelate compound (V) as yellow crystals.

[Step (A4)]

The whole of the crystals obtained as described in Step (A3) above were dissolved in a mixture of 200 ml of 80% aqueous ethanol and 30 ml of triethylamine, and the solution was heated under reflux for 4 hours. The solution was then cooled to room temperature and filtered to remove insoluble material. The filtrate was concentrated by evaporation under reduced pressure, and the crystals obtained were washed with ethanol. The crystals were suspended in 100 ml of ethanol, and 3 ml of concentrated hydrochloric acid were added to the suspension. The solvent in the mixture was then removed by evaporation under reduced pressure. The residue was washed with ethanol to afford 2.7 g of 1-cyclopropyl-6-fluoro-8-methoxy-7-(3-methyl-1-piperazinyl)-1,4-dihydro-4-oxoquinoline-3-carboxylic acid hydrochloride as a colorless powder melting at 262°–264° C. (with decomposition).

Elemental analysis: Calculated for $C_{19}H_{22}FN_3P_4 \cdot HCl$: C, 55.40%; H, 5.63%; N, 10.20%. Found: C, 55.14%; H, 5.67%; N, 10.18%.

EXAMPLE 23

7-(cis-3-Amino-4-methoxy-1-pyrrolidinyl)-1-cyclopropyl-6-fluoro-8-methoxy-1,4-dihydro-4-oxoquinoline-3-carboxylic acid hydrochloride

[Steps (A3)+(A4)]

(a) Following the same procedures as described in Example 22, but using 3.0 g (0.0088 mole) of 1-cyclopropyl-6,7-difluoro-8-methoxy-1,4-dihydro-4-oxoquinoline-3-carboxylic acid boron difluoride chelate (IV) (prepared as described in Preparation 7) and 2.16 g (0.018 mole) of cis-3-amino-4-methoxypyrrolidine (prepared as described in Preparation 8), 1.55 g of 7-(cis-3-amino-4-methoxy-1-pyrrolidinyl)-1-cyclopropyl-6-fluoro-3-methoxy-1,4-dihydro-4-oxoquinoline-3-carboxylic acid was prepared as yellow powdery crystals melting at 242°–245° C.

Mass Spectrum: m/e 391 (M+), 347 (M+-CO2), 360 (M+-OCH3).

(b) 1.5 ml of concentrated hydrochloric acid was added to a suspension of the 7-(cis-3-amino-4-methoxy-1-pyrrolidinyl)-1-cyclopropyl-6-fluoro-3-methoxy-1,4-dihydro-4-oxoquinoline-3-carboxylic acid prepared as described in Step (a) above in 50 ml of ethanol, and the solvent in the mixture was then removed by evaporation under reduced pressure. The residue was washed with ethanol, to afford 1.35 g of the hydrochloride of the title compound as pale yellow powdery crystals melting at 163°–169° C.

Elemental Analysis: Calculated for $C_{19}H_{22}FN_3O_5 \cdot HCl \cdot \frac{1}{4}H_2O$: C, 52.78%; H, 5.45%; N, 9.72%. Found: C, 52.68%; H, 5.64%; N, 9.72%.

EXAMPLES 24+25

Following the same procedure as described in Example 23(b) above, but employing the appropriate acid in place of hydrochloric acid, the following salts were also produced:

EXAMPLE 24

7-(cis-3-amino-4-methoxy-1-pyrrolidinyl)-1-cyclopropyl-6-fluoro-8-methoxy-1,4-dihydro-4-oxoquinoline-3-carboxylic acid methanesulfonate sesquihydrate, melting at 178°–179° C.;

EXAMPLE 25

7-(cis-3-amino-4-methoxy-1-pyrrolidinyl)-1-cyclopropyl-6-fluoro-8-methoxy-1,4-dihydro-4-oxoquinoline-3-carboxylic acid p-toluenesulfonate, melting at 191°–193° C.

EXAMPLE 26

1-Cyclopropyl-6-fluoro-8-methoxy-7-morpholino-1,4-dihydro-4-oxoquinoline-3-carboxylic acid

[Step (A1)]

1.2 g (0.012 mole) of morpholine was added to a solution of 0.9 g (0.003 mole) of 1-cyclopropyl-6,7-difluoro-8-methoxy-1,4-dihydro-4-oxoquinoline-3-carboxylic acid (IIc) (prepared as described in Preparation 6) in 5 ml of dimethyl sulfoxide, and the mixture was stirred at 70° C. for 6 hours. At the end of this time, the solvent and the excess morpholine were removed at the same temperature by evaporation under reduced pressure. The residue was washed with ethyl acetate and then subjected to silica gel column chromatography eluted with methanol, to afford 0.65 g of 1-cyclopropyl-6-fluoro-8-methoxy-7-morpholino-1,4-dihydro-4-oxoquinoline-3-carboxylic acid as a pale brown powder melting at 235°–237° C.

Mass Spectrum: m/e 362 (M+), 318 (M+-CO2).

EXAMPLE 27

1-Cyclopropyl-6-fluoro-8-methoxy-7-(3-hydroxy-1-pyrrolidinyl)-1,4-dihydro-4-oxoquinoline-3-carboxylic acid

[Steps (A2), (A3)+(A4)]

A suspension of 0.50 g (0.0015 mole) of ethyl 1-cyclopropyl-6,7-difluoro-8-methoxy-1,4-dihydro-4-oxoquinoline-3-carboxylate (XXXII) (prepared as described in Preparation 3) in 10 ml of 42% aqueous hydrofluoroboric acid was stirred at 90°–100° C. for 3 hours, and then poured into water to precipitate a crystalline substance. This crystalline substance was collected by filtration to afford 0.55 g of the chelate (IV) as a colorless powder. The whole of this chelate was dissolved in 2.5 ml of dimethyl sulfoxide, and 0.52 g (0.006 mole) of 3-hydroxypyrrolidine was added to the resulting solution. The mixture was then allowed to stand at room temperature overnight. At the end of this time, the reaction mixture was poured into 250 ml of diethyl ether to precipitate yellow crystals, which were collected by filtration. The whole of these crystals was dissolved in a mixture of 150 ml of 80% aqueous ethanol and 25 ml of triethylamine, and the solution was heated under reflux for 4 hours. The solution was then cooled to room temperature, insoluble material was removed by filtration, and the filtrate was concentrated by evaporation under reduced pressure to yield a crystalline substance, which was washed with ethanol. The crude crystals thus obtained were recrystallized from a mixture of methanol and water to afford 0.35 g of 1-cyclopropyl-6-fluoro-8-methoxy-7-(3-hydroxy-1-pyrrolidinyl)-1,4-dihydro-4-oxoquinoline-3-carboxylic acid as pale brown needles melting at 253°–254° C.

Mass Spectrum: m/e 362 (M+), 318 (M+-CO2).

Elemental analysis: Calculated for $C_{18}H_{19}FN_2O_5$: C, 59.67%; H, 5.25%; N, 7.73%. Found: C, 59.74%; H, 5.30%; N, 7.72%.

EXAMPLES 28 TO 37

The following compounds were also prepared according to the same procedures as described in the appropriate one of Example 26 and Example 27.

EXAMPLE 28

1-Cyclopropyl-6-fluoro-8-methoxy-7-thiomorpholino-1,4-dihydro-4-oxoquinoline-3-carboxylic acid, melting at 249°–250° C.

EXAMPLE 29

1-Cyclopropyl-6-fluoro-8-methoxy-7-(3-hydroxy-1-azetidinyl)-1,4-dihydro-4-oxoquinoline-3-carboxylic acid hydrate, melting at 263°–266° C.

EXAMPLE 30

1-Cyclopropyl-6-fluoro-8-methoxy-7-(3-hydroxypiperidino)-1,4-dihydro-4-oxoquinoline-3-carboxylic acid, melting at 239°–241° C.

EXAMPLE 31

1-Cyclopropyl-6-fluoro-8-methoxy-7-(4-hydroxypiperidino)-1,4-dihydro-4-oxoquinoline-3-carboxylic acid, melting at 215°–217° C.

EXAMPLE 32

1-Cyclopropyl-6-fluoro-8-methoxy-7-(3,4-dihydroxy-1-pyrrolidinyl)-1,4-dihydro-4-oxoquinoline-3-carboxylic acid hemihydrate, melting at 236°–239° C.

EXAMPLE 33

1-Cyclopropyl-6-fluoro-8-methoxy-7-(3-hydroxy-4-methoxy-1-pyrrolidinyl)-1,4-dihydro-4-oxoquinoline-3-carboxylic acid hemihydrate, melting at 235°–236° C.

EXAMPLE 34

1-Cyclopropyl-6-fluoro-8-methoxy-7-(3-amino-4-hydroxy-1-pyrrolidinyl)-1,4-dihydro-4-oxoquinoline-3-carboxylic acid hydrochloride sesquihydrate, melting at 218°–220° C. (with decomposition).

EXAMPLE 35

1-Cyclopropyl-6-fluoro-8-methoxy-7-(3-hydroxy-4-methylamino-1-pyrrolidinyl)-1,4-dihydro-4-oxoquinoline-3-carboxylic acid hemihydrate, melting at 240°–241° C. (with decomposition).

EXAMPLE 36

1-Cyclopropyl-6-fluoro-8-methoxy-7-(3-dimethylamino-4-hydroxy-1-pyrrolidinyl)-1,4-dihydro-4-oxoquinoline-3-carboxylic acid hemihydrate, melting at 198°–199° C.

EXAMPLE 37

1-(2-Fluoroethyl)-6-fluoro-8-methoxy-7-(3-hydroxy-1-pyrrolidinyl)-1,4-dihydro-4-oxoquinoline-3-carboxylic acid hemihydrate, melting at 225°–227° C.

EXAMPLE 38

6-Fluoro-1-(2-fluoroethyl)-8-methoxy-7-(4-methyl-1-piperazinyl)-1,4-dihydro-4-oxoquinoline-3-carboxylic acid hydrochloride

[Step (A1)]

0.11 g (0.0004 mole) of 6,7-difluoro-1-(2-fluoroethyl)-8-methoxy-1,4-dihydro-4-oxoquinoline-3-carboxylic acid (prepared as described in Preparation 15) and 0.20 g (0.002 mole) of N-methylpiperazine were dissolved in 3 ml of dimethyl sulfoxide, and the mixture was stirred at 70° C. for 6 hours. At the end of this time, the solvent and excess N-methylpiperazine were distilled off at the same temperature and under reduced pressure, and the residue was washed with ethyl acetate to give a pale-yellow powder. This powder was suspended in a mixture of 20 ml of ethanol and 1 ml of concentrated hydrochloric acid, and the suspension was concentrated by evaporation under reduced pressure. 20 ml of water were added to the residue, and the mixture was filtered to remove insoluble materials. The filtrate was concentrated by evaporation under reduced pressure to give 30 mg of 6-fluoro-1-(2-fluoroethyl)-8-methoxy-7-(4-methyl-1-piperazinyl)-1,4-dihydro-4-oxoquinoline-3-carboxylic acid hydrochloride as a colorless powder melting at 270°–272° C. (with decomposition).

Mass Spectrum: m/e 381 (M+) and 337 (M+-CO$_2$).

Nuclear Magnetic Resonance Spectrum (hexadeuterated dimethyl sulfoxide) δppm: 2.85 (3H, singlet); 4.65–5.10 (4H, multiplet); 7.90 (1H, doublet); 8.90 (1H, singlet).

Elemental analysis: Calculated for $C_{18}H_{21}F_2N_3O_4 \cdot HCl \cdot 2H_2O$: C, 47.63%; H, 5.77%; N, 9.26%. Found: C, 47.95%; H, 5.26%; N, 9.28%.

EXAMPLE 39

1-Ethyl-6-fluoro-8-methoxy-7-(4-methyl-1-piperazinyl)-1,4-dihydro-4-oxoquinoline-3-carboxylic acid boron trifluoride addition product

[Steps (A2), (A3)+(A5)]

0.40 g (0.0013 mole) of ethyl 6,7-difluoro-1-ethyl-8-methoxy-1,4-dihydro-4-oxoquinoline-3-carboxylate (prepared as described in Preparation 16) was suspended in 8 ml of 42% aqueous hydrofluoroboric acid. The suspension was then stirred at 100°–110° C. for 3 hours, after which a precipitated chelate (IV) was collected by filtration, washed with water and dried completely. The chelate (IV) was dissolved in 4 ml of dimethyl sulfoxide, and then 0.7 g (0.007 mole) of N-methylpiperazine were added, and the mixture was allowed to stand overnight at room temperature. At the end of this time, 150 ml of diethyl ether were added to the reaction mixture, and the precipitated yellow crystals of the chelate (V) were collected by filtration. These crystals were suspended in 100 ml of 80% aqueous methanol, and the suspension was heated under reflux, whilst stirring, for 4 hours. At the end of this time, the hot reaction mixture was filtered to remove insoluble materials, and the filtrate was concentrated by evaporation under reduced pressure to give crystals. These were washed with ethanol to give 50 mg of 1-ethyl-6-fluoro-8-methoxy-7-(4-methyl-1-piperazinyl)-1,4-dihydro-4-oxoquinoline-3-carboxylic acid boron trifluoride addition product as a colorless powder melting at 186°–192° C. (with decomposition).

Mass Spectrum: m/e 363 (M+) and 319 (M+-CO$_2$).

Nuclear Magnetic Resonance Spectrum (hexadeuterated dimethyl sulfoxide) δppm: 1.34 (3H, triplet); 2.80 (3H, singlet); 3.85 (3H, singlet); 4.69 (2H, quartet); 7.86 (1H, doublet); 8.90 (1H, singlet).

Elemental analysis: Calculated for $C_{18}H_{22}FN_3O_4 \cdot BF_3$: C, 50.14%; H, 5.14%; N, 9.75%. Found: C, 49.84%; H, 5.44%; N, 9.60%.

EXAMPLE 40

1-Ethyl-6-fluoro-8-methoxy-7-(4-methyl-1-piperazinyl)-1,4-dihydro-4-oxoquinoline-3-carboxylic acid

[Step (A6)]

130 mg (0.0003 mole) of 1-ethyl-6-fluoro-8-methoxy-7-(4-methyl-1-piperazinyl)-1,4-dihydro-4-oxoquinoline- 3-carboxylic acid boron trifluoride addition product (prepared as described in Example 39) were dissolved in 30 ml of water. 0.36 ml of a 1N aqueous solution of sodium hydroxide was added to the solution, and the reaction mixture was concentrated by evaporation under reduced pressure to give crystals. These were recrystallized from ethanol and then washed with cold water, to give 70 mg of 1-ethyl-6-fluoro-8-methoxy-7-(4-methyl-1-piperazinyl)-1,4-dihydro-4-oxoquinoline-3-carboxylic acid as a pale brown powder melting at 207°–209° C. (with decomposition).

Mass Spectrum: m/e 363 (M+) and 319 (M+-CO$_2$).

Nuclear Magnetic Resonance Spectrum (hexadeuterated dimethyl sulfoxide-CDCl$_3$) δppm: 1.34 (3H, triplet); 2.47 (3H, singlet); 3.85 (3H, singlet); 4.69 (2H, quartet); 7.86 (1H, doublet); 8.86 (1H, singlet).

Elemental analysis: Calculated for $C_{18}H_{22}FN_3O_4.3H_2O$: C, 51.79%; H, 6.76%; N, 10.07%. Found: C, 51.89%; H, 6.58%; N, 9.93%.

EXAMPLE 41

1-Ethyl-6-fluoro-8-methoxy-7-(4-methyl-1-piperazinyl)-1,4-dihydro-4-oxoquinoline-3-carboxylic acid

[Step (A4)]

A suspension of 200 mg (0.00046 mole) of the chelate compound (V) (yellow crystals) (prepared as described in Example 39) in 50 ml of 80% aqueous methanol containing 0.5 ml of triethylamine was heated under reflux for 6 hours whilst stirring. The hot reaction mixture was then filtered to remove insoluble materials, and the filtrate was concentrated by evaporation under reduced pressure to give crystals, which were then washed with ethanol. 90 mg of 1-ethyl-6-fluoro-8-methoxy-7-(4-methyl-1-piperazinyl)-1,4-dihydro-4-oxoquinoline-3-carboxylic acid were isolated as a pale brown powder. It was confirmed that the melting point, mass spectrum, nuclear magnetic resonance spectrum and elemental analysis were the same as those of the compound prepared as described in Example 40.

EXAMPLES 42 TO 63

The following compounds were also prepared according to the same procedures as described in the appropriate one of Examples 38, 39, 40 or 41.

EXAMPLE 42

1-Ethyl-6-fluoro-8-methoxy-7-(1-piperazinyl)-1,4-dihydro-4-oxoquinoline-3-carboxylic acid boron trifluoride addition product, melting at 168°–173° C. (with decomposition).

EXAMPLE 43

1-Methyl-6-fluoro-8-methoxy-7-(4-methyl-1-piperazinyl)-1,4-dihydro-4-oxoquinoline-3-carboxylic acid hydrochloride hydrate, melting at 214°–215° C. (with decomposition).

EXAMPLE 44

1-Methyl-6-fluoro-8-methoxy-7-(1-piperazinyl)-1,4-dihydro-4-oxoquinoline-3-carboxylic acid dihydrochloride hydrate, melting at 213°–216° C. (with decomposition).

EXAMPLE 45

1-Methyl-6-fluoro-8-methoxy-7-(4-methyl-1-homopiperazinyl)-1,4-dihydro-4-oxoquinoline-3-carboxylic acid dihydrochloride hemihydrate, melting at 192°–195° C. (with decomposition).

EXAMPLE 46

1-Ethyl-6-fluoro-8-methoxy-7-(3-methyl-1-piperazinyl)-1,4-dihydro-4-oxoquinoline-3-carboxylic acid dihydrate, melting at 145°–151° C.

EXAMPLE 47

1-Ethyl-6-fluoro-8-methoxy-7-(3-dimethylamino-1-pyrrolidinyl)-1,4-dihydro-4-oxoquinoline-3-carboxylic acid hydrochloride boron trifluoride addition product, melting at 185°–187° C.

EXAMPLE 48

1-Ethyl-6-fluoro-8-methoxy-7-(3-methylamino-1-pyrrolidinyl)-1,4-dihydro-4-oxoquinoline-3-carboxylic acid boron trifluoride addition product trihydrate, melting at 201°–204° C.

EXAMPLE 49

1-Ethyl-6-fluoro-8-methoxy-7-(3,4-dimethyl-1-piperazinyl)-1,4-dihydro-4-oxoquinoline-3-carboxylic acid hydrochloride hydrate, melting at 215°–218° C. (with decomposition).

EXAMPLE 50

1-(2-Fluoroethyl)-6-fluoro-8-methoxy-7-(1-piperazinyl)-1,4-dihydro-4-oxoquinoline-3-carboxylic acid dihydrate, melting at 242°–246° C. (with decomposition).

EXAMPLE 51

1-(2-Fluoroethyl)-6-fluoro-8-methoxy-7-(3-methyl-1-piperazinyl)-1,4-dihydro-4-oxoquinoline-3-carboxylic acid, melting at 156°–157° C.

EXAMPLE 52

1-(2-Fluoroethyl)-6-fluoro-8-methoxy-7-(3,4-dimethyl-1-piperazinyl)-1,4-dihydro-4-oxoquinoline-3-carboxylic acid hydrochloride, melting at 241°–247° C. (with decomposition).

EXAMPLE 53

1-(2-Fluoroethyl)-6-fluoro-8-methoxy-7-(3,5-dimethyl-1-piperazinyl)-1,4-dihydro-4-oxoquinoline-3-carboxylic acid hydrochloride, melting above 300° C.

EXAMPLE 54

1-(2-Fluoroethyl)-6-fluoro-8-methoxy-7-(3,4,5-trimethyl-1-piperazinyl)-1,4-dihydro-4-oxoquinoline-3-carboxylic acid hydrochloride hydrate, melting at 262°–270° C. (with decomposition).

EXAMPLE 55

1-(2-Fluoroethyl)-6-fluoro-8-methoxy-7-(3-amino-1-pyrrolidinyl)-1,4-dihydro-4-oxoquinoline-3-carboxylic acid, melting at 164°–167° C.

EXAMPLE 56

1-(2-Fluoroethyl)-6-fluoro-8-methoxy-7-(3-methylamino-1-pyrrolidinyl)-1,4-dihydro-4-oxoquinoline-3-carboxylic acid boron trifluoride addition product hemihydrate. melting at 184°–186° C.

EXAMPLE 57

1-(2-Fluoroethyl)-6-fluoro-8-methoxy-7-(3-ethylamino-1-pyrrolidinyl)-1,4-dihydro-4-oxoquinoline- 3-carboxylic acid boron trifluoride addition product sesquihydrate, melting at 200°–202° C.

EXAMPLE 58

1-(2-Fluoroethyl)-6-fluoro-8-methoxy-7-(3-dimethylamino-1-pyrrolidinyl)-1,4-dihydro-4-oxoquinoline-3-carboxylic acid dihydrate, melting at 179°–182° C.

EXAMPLE 59

1-(2-Fluoroethyl)-6-fluoro-8-methoxy-7-[3-(N-ethyl-N-methylamino)-1-pyrrolidinyl]-1,4-dihydro-4-oxoquinoline-3-carboxylic acid hydrochloride, melting at 171°–173° C.

EXAMPLE 60

1-(2-Fluoroethyl)-6-fluoro-8-methoxy-7-(3-aminomethyl-1-pyrrolidinyl)-1,4-dihydro-4-oxoquinoline-3-carboxylic acid boron trifluoride addition product, melting at 143°–146° C.

EXAMPLE 61

1-(2-Fluoroethyl)-6-fluoro-8-methoxy-7-[3-(N-ethylamino)methyl-1-pyrrolidinyl]-1,4-dihydro-4-oxoquinoline-3-carboxylic acid boron trifluoride addition product, melting at 191°–194° C.

EXAMPLE 62

1-Methylamino-6-fluoro-8-methoxy-7-(1-piperazinyl)-1,4-dihydro-4-oxoquinoline-3-carboxylic acid hydrochloride hemihydrate, melting at 232°–237° C. (with decomposition).

EXAMPLE 63

1-Methylamino-6-fluoro-8-methoxy-7-(4-methyl-1-piperazinyl)-1,4-dihydro-4-oxoquinoline-3-carboxylic acid dihydrochloride, melting at 213°–218° C. (with decomposition).

EXAMPLE 64

7-(trans-3-Amino-4-methoxy-1-pyrrolidinyl)-1-cyclopropyl-6-fluoro-8-methoxy-1,4-dihydro-4-oxoquinoline-3-carboxylic acid hydrochloride

[Steps (A3)+(A4)]

0.19 g (0.0036 mole) of sodium methoxide was added to a suspension of 0.34 g (0.0018 mole) of trans-3-amino-4-methoxypyrrolidine dihydrochloride (prepared as described in Preparation 18) in 1.5 ml of dimethyl sulfoxide, and the mixture was stirred at room temperature for 30 minutes. 0.31 g (0.0009 mole) of a chelate (IV) of 1-cyclopropyl-6,7-difluoro-8-methoxy-1,4-dihydro-4-oxoquinoline-3-carboxylic acid and boron difluoride (prepared as described in Preparation 7) were added to the resulting solution, followed by 0.27 g (0.0027 mole) of triethylamine. The mixture was then allowed to stand at room temperature overnight. At the end of this time, 50 ml of water were added to the mixture, and a chelate (V) separated out. This was collected by filtration to give yellow crystals. These were worked up in a similar manner to that described in Example 22, to give 0.22 g of 7-(trans-3-amino-4-methoxy-1-pyrrolidinyl)-1-cyclopropyl-6-fluoro-8-methoxy-1,4-dihydro-4-oxoquinoline-3-carboxylic acid hydrochloride as a fine yellow powder, melting at 192°–195° C.

Elemental analysis: Calculated for $C_{19}H_{22}FN_3O_5 \cdot HCl \cdot \frac{1}{2}H_2O$: C, 52.24%; H, 5.54%; N, 9.62%. Found C, 52.00%; H, 5.54%; N, 9.58%.

EXAMPLES 65 TO 69

The following compounds were also prepared according to the same procedure as described in Example 64.

EXAMPLE 65

7-(cis-3-Amino-4-ethoxy-1-pyrrolidinyl)-1-cyclopropyl-6-fluoro-8-methoxy-1,4-dihydro-4-oxoquinoline-3-carboxylic acid hydrochloride hemihydrate, melting at 189°–194° C.

EXAMPLE 66

7-(cis-3-Methoxy-4-methylamino-1-pyrrolidinyl)-1-cyclopropyl-6-fluoro-8-methoxy-1,4-dihydro-4-oxoquinoline-3-carboxylic acid hydrochloride hemihydrate, melting at 208°–211° C.

EXAMPLE 67

7-(cis-3-Dimethylamino-4-methoxy-1-pyrrolidinyl)-1-cyclopropyl-6-fluoro-8-methoxy-1,4-dihydro-4-oxoquinoline-3-carboxylic acid hydrochloride hemihydrate, melting at 214°–217° C. (with decomposition).

EXAMPLE 68

7-(cis-3-Amino-4-methoxy-1-pyrrolidinyl)-1-ethyl-6-fluoro-8-methoxy-1,4-dihydro-4-oxoquinoline-3-carboxylic acid hydrochloride hydrate, melting at 204°–207° C.

EXAMPLE 69

7-(cis-3-Amino-4-methoxy-1-pyrrolidinyl)-1-(2-fluoroethyl)-6-fluoro-8-methoxy-1,4-dihydro-4-oxoquinoline-3-carboxylic acid hydrochloride hemihydrate, melting at 180°–183° C.

EXAMPLE 70

7-(cis-3-Benzylamino-4-methoxy-1-pyrrolidinyl)-1-cyclopropyl-6-fluoro-8-methoxy-1,4-dihydro-4-oxoquinoline-3-carboxylic acid hydrochloride sesquihydrate, melting at 156°–159° C.

EXAMPLE 71

7-(3-Amino-4-methyl-1-pyrrolidinyl)-1-cyclopropyl-6-fluoro-8-methoxy-1,4-dihydro-4-oxoquinoline-3-carboxylic acid hydrochloride, melting at 179°–181° C.

EXAMPLE 72

6-Fluoro-1-(4-fluorophenyl)-8-methoxy-7-(1-piperazinyl)-1,4-dihydro-4-oxoquinoline-3-carboxylic acid hydrochloride

[Steps (A2), (A3)+(A4)]

(a) A suspension of 1.0 g (0.0027 mole) of ethyl 6,7-difluoro-1-(4-fluorophenyl)-8-methoxy-1,4-dihydro-4-oxoquinoline-3-carboxylate (XXXII, $R^{11}$=4-fluorophenyl) (prepared as described in Preparation 4) in 15 ml of 42% aqueous hydrofluoroboric acid was stirred at 90°–100° C. for 3 hours, after which it was poured into water. The precipitated crystals were collected by filtration to give 1 g of a chelate (IV) as a colorless powder. The whole of this was dissolved in 3 ml of dimethyl sulfoxide, and the solution was mixed with 0.43 g (0.005 mole) of anhydrous piperazine. The mixture was then stirred at 60°–70° C. for 3 hours. At the end of this time, the reaction mixture was allowed to cool to room temperature. On adding water, a chelate (V) separated out as yellow crystals, which were collected by filtration.

The crystals were dissolved in a mixture of 150 ml of 80% aqueous methanol and 5 ml of triethylamine, and the solution was heated under reflux for 4 hours. It was then allowed to cool to room temperature, and insoluble materials were removed by filtration. The filtrate was then concentrated by evaporation under reduced pressure to give crystals. These were washed with ethanol to give 0.73 g of 6-fluoro-1-(4-fluorophenyl)-8-methoxy-7-(1-piperazinyl)-1,4-dihydro-4-oxoquinoline-3-carboxylic acid as a colorless powder.

(b) The whole of the crystals obtained as described in Step (a) above were suspended in 100 ml of ethanol, and then 1 ml of concentrated hydrochloric acid was added to the suspension. The suspension was then heated to boiling, whilst stirring, after which it was filtered to give 0.47 g of the hydrochloride of the title compound as a colorless powder, melting point: above 265° C. (with decomposition).

EXAMPLES 73 TO 83

The following compounds were also prepared according to the same procedure as described in Example 72.

EXAMPLE 73

6-Fluoro-1-(4-fluorophenyl)-8-methoxy-7-(4-methyl-1-piperazinyl)-1,4-dihydro-4-oxoquinoline-3-carboxylic acid hydrochloride hydrate, melting at 250°-255° C. (with decomposition).

EXAMPLE 74

6-Fluoro-1-(4-fluorophenyl)-8-methoxy-7-(3-methyl-1-piperazinyl)-1,4-dihydro-4-oxoquinoline-3-carboxylic acid hydrochloride hemihydrate, melting at 246°-249° C. (with decomposition).

EXAMPLE 75

6-Fluoro-1-(2,4-difluorophenyl)-8-methoxy-7-(1-piperazinyl)-1,4-dihydro-4-oxoquinoline-3-carboxylic acid hydrochloride hydrate, melting at above 284° C. (with gradual decomposition).

EXAMPLE 76

6-Fluoro-1-(2,4-difluorophenyl)-8-methoxy-7-(4-methyl-1-piperazinyl)-1,4-dihydro-4-oxoquinoline-3-carboxylic acid hydrochloride hemihydrate, melting at 287°-291° C. (with decomposition).

EXAMPLE 77

6-Fluoro-1-(2,4-difluorophenyl)-8-methoxy-7-(3-methyl-1-piperazinyl)-1,4-dihydro-4-oxoquinoline-3-carboxylic acid hydrochloride hemihydrate, melting at 279°-285° C. (with decomposition).

EXAMPLE 78

1-Cyclopropyl-7-[3-(ethylamino)methyl-1-pyrrolidinyl]-6-fluoro-8-methoxy-1,4-dihydro-4-oxoquinoline-3-carboxylic acid hydrochloride, melting at 243°-245° C.

EXAMPLE 79

7-(3-Aminomethyl-3-hydroxy-1-pyrrolidinyl)-1-cyclopropyl-6-fluoro-8-methoxy-1,4-dihydro-4-oxoquinoline-3-carboxylic acid hydrochloride sesquihydrate, melting at 205°-209° C.

EXAMPLE 80

7-(3-Amino-1-pyrrolidinyl)-6-fluoro-1-(4-fluorophenyl)-8-methoxy-1,4-dihydro-4-oxoquinoline-3-carboxylic acid hydrochloride sesquihydrate, melting at 180°-185° C.

EXAMPLE 81

7-(cis-3-Amino-4-methoxy-1-pyrrolidinyl)-6-fluoro-1-(4-fluorophenyl)-8-methoxy-1,4-dihydro-4-oxoquinoline-3-carboxylic acid hydrochloride 5/2 hydrate, melting at 196°-201° C.

EXAMPLE 82

7-(3-Amino-1-pyrrolidinyl)-1-(2,4-difluorophenyl)-6-fluoro-8-methoxy-1,4-dihydro-4-oxoquinoline-3-carboxylic acid hydrochloride dihydrate, melting at 193°-197° C.

EXAMPLE 83

7-(cis-3-Amino-4-methoxy-1-pyrrolidinyl)-1-(2,4-difluorophenyl)-6-fluoro-8-methoxy-1,4-dihydro-4-oxoquinoline-3-carboxylic acid hydrochloride sesquihydrate, melting at 221°-223° C.

PREPARATION 1

3-Methoxy-2,4,5-trifluorobenzoic acid (XXVI)

Step (F1):
4-Methoxy-2-phthalimido-3,5,6-trifluoro-1-nitrobenzene (XXXIV)

4.62 g (0.025 mole) of potassium phthalimide were added to a solution of 5.41 g (0.024 mole) of 4-methoxy-2,3,5,6-tetrafluoro-1-nitrobenzene (XXXIII) in 100 ml of dimethylformamide, and the mixture was stirred at room temperature for 3 hours. At the end of this time, the solvent was removed by evaporation under reduced pressure, the residue was dissolved in toluene, and the solution was washed with water, dried and concentrated by evaporation under reduced pressure to give an oily substance. This oily substance was subjected to silica gel column chromatography eluted with toluene, to afford 5.07 g of 4-methoxy-2-phthalimido-3,5,6-trifluoro-1-nitrobenzene (XXXIV) as pale yellow powdery crystals.

Mass Spectrum: m/e 352 (M+), 306 (M+-NO$_2$), 291 (M+-NO$_2$—CH$_3$).

Step (F2):
4-Methoxy-2-phthalimido-3,5,6-trifluoroaniline (XXXV)

1.3 g of 5% w/w palladium-on-carbon was added to a solution of 4.2 g (0.012 mole) of 4-methoxy-2-phthalimido-3,5,6-trifluoro-1-nitrobenzene (XXXIV) [prepared as described in Step (F1) above] in 150 ml of acetic acid, and the mixture was agitated vigorously for 1 hour in an atmosphere of hydrogen. At the end of this time, the reaction mixture was filtered, the filtrate was concentrated by evaporation under reduced pressure, and the solid which separated was washed with toluene, to afford 2.93 g of 4-methoxy-2-phthalimido-3,5,6-trifluoroaniline (XXXV) as colorless sandy crystals.

Mass Spectrum: m/e 322 (M+), 307 (M+-CH$_3$).

Step (F3): N-(3-Methoxy-2,4,5-trifluorophenyl)-phthalimide (XXXVI)

A solution of 2.90 g (0.009 mole) of 4-methoxy-2-phthalimido-3,5,6-trifluoroaniline (XXXV) [prepared as described in Step (F2) above] in 18 ml of dimethylformamide was added dropwise, whilst stirring at 60°–65° C., to a solution of 1.66 g (0.0144 mole) of isoamyl nitrite in 9 ml of dimethylformamide. After the addition was complete, the reaction mixture was stirred at the same temperature for 1 hour, and then the solvent was removed by evaporation under reduced pressure. The residue was subjected to silica gel column chromatography eluted with toluene, to afford 2.18 g of N-(3-methoxy-2,4,5-trifluorophenyl)phthalimide (XXXVI) as colorless powdery crystals.

Mass Spectrum: m/e 307 (M+), 276 (M+-OCH$_3$).

Step (F4): 3-Methoxy-2,4,5-trifluoroaniline (XXIII)

1.1 g (0.02 mole) of hydrazine hydrate was added to a suspension of 2.15 g (0.007 mole) of N-(3-methoxy-2,4,5-trifluorophenyl)phthalimide (XXXVI) [prepared as described in Step (F3) above] in 30 ml of ethanol, and the mixture was heated under reflux with stirring for 2 hours. The reaction mixture was cooled to room temperature and then filtered. The filtrate was concentrated by evaporation under reduced pressure, and the residue was dissolved in toluene. The resulting solution was washed with water and dried, and the solvent was then removed by evaporation under reduced pressure to afford 1.06 g of 3-methoxy-2,4,5-trifluoroaniline (XXIII) as pale brown needles.

Mass Spectrum: m/e 177 (M+), 147 (M+-CH$_2$=O).

Step (F5)=Step (E4): 3-Methoxy-2,4,5-trifluorobenzonitrile (XXIV)

(a) A solution of 1.01 g (0.0056 mole) of 3-methoxy-2,4,5-trifluoroaniline (XXIII) [prepared as described in Step (F4) above] in a mixture of 3 ml of acetic acid, 2.5 ml of water and 1.68 g (0.0168 mole) of concentrated sulfuric acid was cooled to 0° C., and then 1 ml of an aqueous solution containing 0.46 g (0.0066 mole) of sodium nitrite was added dropwise thereto at 0°–3° C., whilst stirring. After the addition was complete, the reaction mixture was stirred for a further 30 minutes at the same temperature to obtain a diazonium salt solution. (b) Meanwhile, 5 ml of an aqueous solution containing 1.95 g (0.03 mole) of potassium cyanide was added dropwise to a solution of 1.80 g (0.0072 mole) of cupric sulfate pentahydrate in 10 ml of water, whilst stirring and at below 20° C., to obtain a brown transparent solution, and 4.02 g (0.048 mole) of sodium bicarbonate and 30 ml of benzene were added, in that order, thereto, to produce a two-layer solution. The diazonium salt solution prepared as described in Step (F5) (a) above was added dropwise to the two-layer solution, with vigorous stirring at 30°–45° C. After the addition was complete, the reaction mixture was warmed up to 65° C. and then cooled to room temperature. The benzene layer was separated, washed with water and dried, and the solvent was removed by evaporation under reduced pressure. The residue was subjected to silica gel column chromatography eluted with toluene, to afford 0.77 g of 3-methoxy-2,4,5-trifluorobenzonitrile (XXIV) as a red oily substance.

Infrared Absorption Spectrum (liquid film) $\nu_{max}$cm$^{-1}$: 2250, 1620, 1500, 1480, 1120, 1080.

Step (F6): 3-Methoxy-2,4,5-trifluorobenzoic acid (XXVI)

5 ml of concentrated sulfuric acid and 1.2 ml of water were added to 1.24 g (0.007 mole) of 3-methoxy-2,4,5-trifluorobenzonitrile (XXIV) [prepared as described in Step (F5) above]. The resulting mixture was heated at 100°–140° C. for 30 minutes, poured into ice-water, and extracted with ethyl acetate. The extract was washed with water and dried, and the solvent was removed by evaporation under reduced pressure. 1.7 ml of concentrated sulfuric acid was added to the residue, and then 4 ml of an aqueous solution containing 0.8 g of sodium nitrite were added dropwise thereto, whilst ice-cooling. The reaction mixture was then heated at 90°–100° C. for 30 minutes, after which it was extracted with chloroform. The extract was washed with water and dried, and the solvent was removed by evaporation under reduced pressure to afford 1.17 g of 3-methoxy-2,4,5-trifluorobenzoic acid (XXVI) as colorless powdery crystals melting at 115°–117° C.

Mass Spectrum: m/e 206 (M+), 189 (M+—OH), 161 (M+-COOH).

Nuclear Magnetic Resonance Spectrum (CDCl$_3$) δppm: 4.09 (3H, singlet); 7.50–7.62 (1H, multiplet); 8.0–10.0 (1H, broad).

PREPARATION 2

3-Methoxy-2,4,5-trifluorobenzoic acid (XXVI)

Step (E1) 4-methoxy-2,3,5,6-tetrafluorobenzonitrile (XIX)

A solution of 44.8 g (0.83 mole) of sodium methoxide in 1.6 liters of methanol was added dropwise at room temperature to a solution of 160.0 g (0.83 mole) of pentafluorobenzonitrile (XVIII) in 2.5 liters of methanol, whilst stirring. When the addition was complete, the mixture was allowed to stand at room temperature overnight. At the end of this time, the solvent was removed by evaporation under reduced pressure, and the residue was shaken with a mixture of water and toluene. The toluene layer was separated, washed with water and dried over anhydrous sodium sulfate; the solvent was then removed by evaporation under reduced pressure. The residual solid was washed with hexane to afford 160.7 g of 4-methoxy-2,3,5,6-tetrafluorobenzonitrile (XIX) as colorless needles.

Mass Spectrum: m/e 205 (M+), 190 (M+-CH$_3$), 162 (M+-CH$_3$—CO).

Step (E2) 2-amino-4-methoxy-3,5,6-trifluorobenzonitrile (XX)

150 ml of liquid ammonia and 100.0 g (0.49 mole) of 4-methoxy-2,3,5,6-tetrafluorobenzonitrile (XIX) [prepared as described in Step (E1) above] were placed in an autoclave, and the mixture was allowed to stand at room temperature overnight. The ammonia was then evaporated off, and the solid obtained was washed with water to afford 84.4 g of 2-amino-4-methoxy-3,5,6-trifluorobenzonitrile (XX) as a colorless powder.

Mass Spectrum: m/e 202 (M+), 172 (M+-CH$_2$=O), 159 (M+-CH$_3$—CO).

Step (E3) 3-methoxy-2,4,5-trifluoroaniline (XXIII)

50 ml of water and 200 ml of concentrated sulfuric acid were added to 84.4 g (0.42 mole) of 2-amino-4-methoxy-3,5,6-trifluorobenzonitrile (XX) [prepared as described in Step (E2) above]. The mixture was then stirred at 100° C. for 1 hour, after which 150 ml of water were added thereto, and the mixture was stirred at 110°–120° C. for a further 2 hours. The reaction mixture was then allowed to stand to cool to room temperature, after which it was poured into ice-water and neutralized with potassium carbonate. The crystalline substance which precipitated was extracted with ethyl acetate; the extract was washed with water and dried over anhydrous sodium sulfate; and the solvent was removed by evaporation under reduced pressure to afford 57.6 g of 3-methoxy-2,4,5-trifluoroaniline (XXIII) as colorless needles melting at 45°–47° C.

Mass Spectrum: m/e 177 (M+), 147 (M+-CH$_2$=O).

Nuclear Magnetic Resonance Spectrum (CDCl$_3$) δppm: 3.65 (2H, broad); 4.02 (3H, singlet); 6.22–6.36 (1H, multiplet).

Step (E4) 3-methoxy-2,4,5-trifluorobenzonitrile (XXIV)

The title compound was prepared as described in Step (F5) of Preparation 1, and had the same properties as the product of Step (F5) of Preparation 1.

Step (E5) 3-methoxy-2,4,5-trifluorobenzamide (XXV)

5 ml of concentrated sulfuric acid and 1.2 ml of water were added to 1.24 g (0.007 mole) of 3-methoxy-2,4,5-trifluorobenzonitrile (XXIV) [prepared as described in Step (E4) above], and the mixture was heated at 100°–140° C. for 30 minutes, poured into ice-water, and extracted with ethyl acetate. The extract was washed with water and dried, and the solvent was removed by evaporation under reduced pressure to afford 1.10 g of 3-methoxy-2,4,5-trifluorobenzamide (XXV) as a pale brown powder melting at 131°–133° C.

Mass Spectrum: m/e 205 (M+), 189 (M+-NH$_2$).

Step (E6) 3-methoxy-2,4,5-trifluorobenzoic acid (XXVI)

226 ml (0.226 mole) of a 1N aqueous solution of sodium hydroxide were added to a suspension of 46.4 g (0.226 mole) of 3-methoxy-2,4,5-trifluorobenzamide (XXV) [prepared as described in Step (E5) above] in 900 ml of water, and the mixture was heated under reflux with stirring for 2 hours. At the end of this time, the reaction mixture was cooled to room temperature and then shaken with ethyl acetate to remove unreacted material. The aqueous layer was separated and acidified with hydrochloric acid to precipitate a crystalline substance, which was extracted with ethyl acetate. The extract was washed with water and dried, and the solvent was removed by evaporation under reduced pressure to afford 37.1 g of 3-methoxy-2,4,5-trifluorobenzoic acid (XXVI) as colorless needles having the same properties as the product of Preparation 1.

PREPARATION 3

Ethyl 1-cyclopropyl-6,7-difluoro-8-methoxy-1,4-dihydro-4-oxoquinoline-3-carboxylate (XXXII)

Steps (E7), (E8) and (E9) ethyl 3-methoxy-2,4,5-trifluorobenzoylacetate (XXIX)

To a solution of 1.14 g (0.0055 mole) of 3-methoxy-2,4,5-trifluorobenzoic acid (XXVI) (prepared as described in Preparation 1 or 2) in 10 ml of dry benzene was added 5 ml of thionyl chloride and the mixture was heated under reflux for 1 hour. At the end of this time, benzene and the excess of thionyl chloride were removed completely to give 3-methoxy-2,4,5-trifluorobenzoyl chloride (XXVII) [Step (E7)].

Meanwhile, a solution of 0.68 g (0.006 mole) of magnesium ethoxide and 0.96 g (0.006 mole) of diethyl malonate in 15 ml of anhydrous diethyl ether was heated under reflux for 1 hour to prepare a suspension of ethoxymagnesium diethyl malonate in diethyl ether. A solution of the 3-methoxy-2,4,5-trifluorobenzoyl chloride (XXVII) obtained as described above in 10 ml of diethyl ether was then added dropwise at room temperature with stirring to the suspension, and the mixture was stirred at room temperature for a further 1 hour. At the end of this time, the reaction mixture was acidified by adding 1N aqueous hydrochloric acid and extracted with ethyl acetate. The extract was washed with water and dried, and the solvent was removed by evaporation under reduced pressure to give 1.8 g of diethyl 3-methoxy-2,4,5-trifluorobenzoylmalonate (XXVIII) as a brown oily substance [Step (E8)].

The whole of this oily substance was dissolved in 30 ml of dioxane, a catalytic amount of p-toluenesulfonic acid was added thereto, and the mixture was heated under reflux for 20 hours. At the end of this time, the solvent was removed by evaporation under reduced pressure to give a residue, which was extracted with ethyl acetate. The extract was washed with an aqueous solution of sodium bicarbonate and with water, in that order, and was then dried. The solvent was then removed by evaporation under reduced pressure to afford 1.45 g of ethyl 3-methoxy-2,4,5-trifluorobenzoylacetate (XXIX) as a pale brown oily substance [Step (E9)].

Mass Spectrum: m/e 276 (M+), 189 (M+-CH$_2$COOC$_2$H$_5$), 161 (M+-COCH$_2$COOC$_2$H$_5$).

Steps (E10) and (E11) ethyl 3-cyclopropylamino-2-(3-methoxy-2,4,5-trifluorobenzoyl)acrylate (XXXI)

3.5 ml of acetic anhydride and 1.1 ml of ethyl orthoformate were added to 1.40 g (0.005 mole) of ethyl 3-methoxy-2,4,5-trifluorobenzoylacetate (XXIX) [prepared as described in Step (E9) above], and the mixture was heated under reflux for 1 hour and then concentrated by evaporation under reduced pressure. 0.38 g (0.006 mole) of cyclopropylamine was added dropwise, whilst ice-cooling and stirring, to a solution of the residue in 10 ml of methylene chloride, and the mixture was stirred for a further 30 minutes. The solvent was then removed by evaporation under reduced pressure from the reaction mixture, and the residue was subjected to silica gel column chromatography eluted with a 9:1 by volume mixture of toluene and ethyl acetate, to afford 1.23 g of ethyl 3-cyclopropylamino-2-(3-methoxy-2,4,5-trifluorobenzoyl)acrylate (XXXI) as a pale brown oily substance.

Mass Spectrum: m/e 343 (M+), 189 (M+-cPrNH—CH=C—COOEt).

Step (E12) ethyl 1-cyclopropyl-6,7-difluoro-8-methoxy-1,4-dihydro-4-oxoquinoline-3-carboxylate (XXXII)

150 mg (0.0035 mole) of sodium hydride (as a 60% w/w dispersion in mineral oil) were added to a solution of 1.20 g (0.0035 mole) of ethyl 3-cyclopropylamino-2-(3-methoxy-2,4,5-trifluorobenzoyl)acrylate (XXXI) [prepared as described in Step (E11) above] in 30 ml of anhydrous tetrahydrofuran, and the mixture was stirred at room temperature for 30 minutes. At the end of this time, the reaction mixture was acidified by adding 1N aqueous hydrochloric acid, and the mixture was extracted with ethyl acetate. The extract was washed with water and dried, and the solvent was removed by evaporation under reduced pressure to afford 0.83 g of ethyl 1-cyclopropyl-6,7-difluoro-8-methoxy-1,4-dihydro-4-oxoquinoline-3-carboxylate (XXXII) as colorless needles, melting at 180°–182° C.

Mass Spectrum: m/e 323 (M+), 251 (M+-COOEt), 41 ($C_3H_5^+$).

PREPARATIONS 4+5

The following compounds were also prepared by following the same procedures as described in Preparation 3:

PREPARATION 4

Ethyl 6,7-difluoro-1-(4-fluorophenyl)-8-methoxy-1,4-dihydro-4-oxoquinoline-3-carboxylate, melting at 222°–226° C.

PREPARATION 5

Ethyl 1-(2,4-difluorophenyl)-6,7-difluoro-8-methoxy-1,4-dihydro-4-oxoquinoline-3-carboxylate, melting at 185°–189° C.

PREPARATION 6

1-Cyclopropyl-6,7-difluoro-8-methoxy-1,4-dihydro-4-oxoquinoline-3-carboxylic acid (IIc) [Step (E13)]

10 ml of a 4% w/v aqueous solution of sodium hydroxide were added to a solution of 0.48 g (0.0015 mole) of ethyl 1-cyclopropyl-6,7-difluoro-8-methoxy-1,4-dihydro-4-oxoquinoline-3-carboxylate (XXXII) (prepared as described in Preparation 3) in 20 ml of methanol, and the mixture was allowed to stand at room temperature for 5 hours. The reaction mixture was then acidified by adding concentrated hydrochloric acid to precipitate a crystalline substance, which was collected by filtration to afford 0.34 g of 1-cyclopropyl-6,7-difluoro-8-methoxy-1,4-dihydro-4-oxoquinoline-3-carboxylic acid (IIC) as colorless powdery crystals melting at 184°–185° C.

Mass Spectrum: m/e 295 (M+), 251 (M+-$CO_2$).

Elemental analysis: Calculated for $C_{14}H_{11}F_2NO_4$: C, 56.95%; H, 3.76%; N, 4.75%. Found: C, 56.90%; H, 3.84%; N, 4.56%.

PREPARATION 7

1-Cyclopropyl-6,7-difluoro-8-methoxy-1,4-dihydro-4-oxoquinoline-3-carboxylic acid boron difluoride chelate (IV) [Step (A2)]

A suspension of 1.0 g (0.003 mole) of ethyl 1-cyclopropyl-6,7-difluoro-8-methoxy-1,4-dihydro-4-oxoquinoline-3-carboxylate (XXXII) (prepared as described in Preparation 3) in 20 ml of 42% aqueous hydrofluoroboric acid was stirred at 90°–100° C. for 3 hours, after which the reaction mixture was poured into water, and the crystals which precipitated were collected by filtration to afford 1.1 g of 1-cyclopropyl-6,7-difluoro-8-methoxy-1,4-dihydro-4-oxoquinoline-3-carboxylic acid boron difluoride chelate (IV) as colorless powdery crystals melting at 224°–226° C.

Elemental analysis: Calculated for $C_{14}H_{10}BF_4NO_4$: C, 49.01%; H, 2.94%; N, 4.08%. Found: C, 49.24%; H, 3.01%; N, 3.79%.

PREPARATION 8 cis-3-Amino-4-methoxypyrrolidine (a) 21.8 g (0.1 mole) of di-t-butyl dicarbonate were added in portions to a solution of 6.91 g (0.1 mole) of 3-pyrroline in 100 ml of methylene chloride, whilst water-cooling, and then the reaction mixture was stirred at room temperature for 7 hours. At the end of this time, the solvent was removed by evaporation under reduced pressure to afford 17.0 g of 1-t-butoxycarbonyl-3-pyrroline as a faintly yellow oily substance.

Mass Spectrum (CI): m/e 170 (M++1).

Infrared Absorption Spectrum (Capillary) $\nu_{max}$ cm$^{-1}$: 2990, 2870, 1710–1690, 1625, 1400, 1170, 1120.

(b) 2.96 g (0.012 mole) of 70% aqueous m-chloroperbenzoic acid were added to a solution of 1.69 g (0.01 mole) of 1-t-butoxycarbonyl-3-pyrroline [prepared as described in Step (a) above] in 10 ml of chloroform, whilst ice-cooling, and the mixture was stirred with ice-cooling for 8 hours and then with water-cooling for 15 hours. At the end of this time, the reaction mixture was extracted with toluene and the extract was washed, in turn, with an aqueous solution of sodium bicarbonate, a 0.1N aqueous solution of sodium thiosulfate and water. It was then dried over anhydrous sodium sulfate, and the solvent was removed by evaporation under reduced pressure. The residue was subjected to silica gel column chromatography eluted with a 1:5 by volume mixture of ethyl acetate and toluene, to afford 1.09 g of 1-t-butoxycarbonyl-3,4-epoxypyrrolidine as a colorless oily substance.

Mass Spectrum (CI): m/e 186 (M++1).

Infrared Absorption Spectrum (Capillary) $\nu_{max}$ cm$^{-1}$: 2990, 2880, 1710–1690, 1420, 1390, 1180, 1120.

(c) 0.30 g (0.0055 mole) of sodium methoxide was added to a solution of 1.02 g (0.0055 mole) of 1-t-butoxycarbonyl-3,4-epoxypyrrolidine [prepared as described in Step (b) above] in 20 ml of anhydrous methanol, and the mixture was heated under reflux for 10 hours. The reaction mixture was then diluted with water and extracted with chloroform. The extract was washed with water and dried, and the solvent was removed by evaporation under reduced pressure to give a residue, which was subjected to silica gel column chromatography eluted with a 1:2 by volume mixture of ethyl acetate and toluene, to afford 0.73 g of 1-t-butoxycarbonyl-3-hydroxy-4-methoxypyrrolidine as a colorless oily substance.

Mass Spectrum: m/e 217 (M+), 57 ($C_4H_9^+$).

Nuclear Magnetic Resonance Spectrum (CDCl$_3$) δppm: 1.46 (9H, singlet); 3.38 (3H, singlet); 3.40–3.62 (4H, multiplet); 3.71 (1H, broad); 4.27 (1H, broad).

(d) 11.5 g (0.1 mole) of methanesulfonyl chloride were added dropwise, whilst ice-cooling to a solution of 13.0 g (0.06 mole) of 1-t-butoxycarbonyl-3-hydroxy-4-methoxypyrrolidine [prepared as described in Step (c) above] in 100 ml of pyridine, and the mixture was stirred overnight whilst ice-cooling. The reaction mixture was then poured into 800 ml of water and extracted with diethyl ether. The extract was washed with water and dried, and the solvent was removed by evaporation under reduced pressure to afford 12.9 g of 1-t-butoxycarbonyl-3-hydroxy-4-methanesulfonyloxypyrrolidine as a brown oily substance. The whole of this oily substance was placed in a 100 ml stainless steel autoclave, and 50 ml of liquid ammonia was added thereto. The mixture was then heated with stirring at 140° C. under pressure for 8 hours. At the end of this time, the excess ammonia was removed by evaporation, and the residue was subjected to silica gel column chromatography eluted with ethanol, to afford 8.0 of cis-3-amino-1-t-butoxycarbonyl-4-methoxypyrrolidine as a brown oily substance.

Mass Spectrum (CI): m/e 217 (M++1), 201 (M+-CH$_3$), 184 (M+-CH$_3$OH), 161 (M+-CH$_2$=C(CH$_3$)$_2$).

Infrared Absorption Spectrum (Capillary) $\nu_{max}$ cm$^{-1}$: 3400, 2990, 2950, 1680, 1410, 1170, 1100.

Nuclear Magnetic Resonance Spectrum (CDCl$_3$) $\delta$ppm: 1.46 (9H, singlet); 1.56 (2H, broad); 2.96–3.16 (1H, multiplet); 3.40 (3H, singlet); 3.40–3.60 (4H, multiplet); 3.60–3.70 (1H, multiplet).

(e) 64 ml of 6N aqueous hydrochloric acid were added to a solution of 4.16 g (0.019 mole) of 3-amino-1-t-butoxycarbonyl-4-methoxypyrrolidine in 200 ml of ethanol, and the mixture was heated under reflux for 1 hour. At the end of this time, the solvent was completely removed by evaporation to dryness under reduced pressure to obtain cis-3-amino-4-methoxypyrrolidine dihydrochloride as a brown powder. The whole of this dihydrochloride was dissolved in 20 ml of water, 1.97 g (0.037 mole) of sodium methoxide was added thereto, and the solvent was removed by evaporation under reduced pressure to give a residue, which was washed with a 1:1 by volume mixture of ethanol and ethyl acetate. The washings were concentrated by evaporation under reduced pressure to afford 2.06 g of cis-3-amino-4-methoxypyrrolidine as a brown oily substance.

Mass Spectrum: m/e 116 (M+), 99 (M+-NH$_3$), 84 (M+-CH$_3$OH).

PREPARATIONS 9 TO 12

The following compounds were also prepared by following the same procedures as described in Preparation 8:

PREPARATION 9 cis-3-Amino-4-ethoxypyrrolidine.

PREPARATION 10 cis-3-Methoxy-4-methylaminopyrrolidine.

PREPARATION 11 cis-3-Dimethylamino-4-methoxypyrrolidine.

PREPARATION 12 cis-3-Benzylamino-4-methoxypyrrolidine.

PREPARATION 13

Steps (B1)+(B2) 3,4-Difluoro-2-methoxyaniline (VIII)

(a) 20 g (0.114 mole) of 2,3-difluoro-6-nitrophenol (VI) were dissolved in 700 ml of acetone. 18.9 g (0.137 mole) of potassium carbonate and 34.1 g (0.24 mole) of methyl iodide were added to the solution, and the mixture was heated under reflux for 20 hours, whilst stirring. The solvent was then removed from the mixture by evaporation under reduced pressure, and the residue was extracted with ethyl acetate. The ethyl acetate extract was washed with water and dried, and the solvent was removed by evaporation under reduced pressure to give 23.0 g of 3,4-difluoro-2-methoxy-1-nitrobenzene (VII) as a yellow oil [Step (B1)].

Mass Spectrum: m/e 189 (M+) and 159 (M+-CH$_2$=O).

(b) 22.6 g (0.422 mole) of ammonium chloride and 38.2 g of reduced iron were added to a solution of 23.0 g (0.114 mole) of 3,4-difluoro-2-methoxy-1-nitrobenzene (VII) [prepared as described in step (a) above] in 1 liter of 80% aqueous methanol. The mixture was then heated under reflux for 4 hours, whilst stirring. At the end of this time, the reaction mixture was filtered, and the filtrate was concentrated by evaporation under reduced pressure. The residue was extracted with toluene. The toluene extract was washed with water, dried, and concentrated by evaporation under reduced pressure to give 10.2 g of 3,4-difluoro-2-methoxyaniline (VIII) as a reddish-brown oil [Step (B2)].

Mass Spectrum: m/e 159 (M+) and 144 (M+-CH$_3$).

PREPARATION 14

Ethyl 6,7-difluoro-8-methoxy-1-methyl-1,4-dihydro-4-oxoquinoline-3-carboxylate (X)

Step (B3) ethyl 6,7-difluoro-4-hydroxy-8-methoxyquinoline-3-carboxylate (IX)

2.84 g (0.013 mole) of diethyl ethoxymethylenemalonate were added to 1.74 g (0.011 mole) of 3,4-difluoro-2-methoxyaniline (VIII) (prepared as described in Preparation 13). The mixture was then stirred at 140°–150° C. for 3 hours, after which 20 ml of diphenyl ether were added, and the mixture was stirred at 240°–250° C. for 1 hour. At the end of this time, the mixture was allowed to cool to room temperature, and then hexane was added to precipitate crystals, which were collected by filtration. 1.60 g of ethyl 6,7-difluoro-4-hydroxy-8-methoxyquinoline-3-carboxylate (IX) were obtained as colorless crystals.

Mass Spectrum: m/e 283 (M+) and 237 (M+-C$_2$H$_5$OH).

Step (B4) ethyl 6,7-difluoro-8-methoxy-1-methyl-1,4-dihydro-4-oxoquinoline-3-carboxylate (X, R$^{9'}$=methyl)

1.60 g (0.0057 mole) of ethyl 6,7-difluoro-4-hydroxy-8-methoxyquinoline-3-carboxylate (IX) [prepared as described in step (B3) above] were dissolved in 20 ml of dimethylformamide, and 1.20 g (0.0085 mole) of potassium carbonate and 2.40 g (0.017 mole) of methyl iodide were added to the resulting solution. The mixture was then stirred at 60°–65° C. for 17 hours. At the end of this time, the solvent was distilled off under reduced pressure. The residue was extracted with methylene chloride, and the methylene chloride extract was washed with water, dried and concentrated by evaporation under reduced pressure to give 1.60 g of ethyl 6,7-difluoro-8-methoxy-1-methyl-1,4-dihydro-4-oxoquinoline-3-carboxylate (X, R$^{9'}$=methyl) as a pale brown powder.

Mass Spectrum: m/e 297 (M+) and 225 (M+-CH=CH—CO$_2$).

PREPARATION 15

6,7-Difluoro-1-(2-fluoroethyl)-8-methoxy-1,4-dihydro-4-oxoquinoline-3-carboxylic acid (IIa, $R^{9'}$=fluoroethyl)

Step (C1)
3,4-difluoro-2-methoxy-N-(trifluoroacetyl)aniline (XI)

16.2 g (0.077 mole) of trifluoroacetic anhydride were added dropwise to a solution of 10.2 g, (0.064 mole) of 3,4-difluoro-2-methoxyaniline (VIII) (prepared as described in Preparation 13) dissolved in 100 ml of toluene, whilst ice-cooling. After the whole of the trifluoroacetic anhydride had been added, the mixture was stirred at room temperature for 2 hours and then concentrated by evaporation under reduced pressure to give 13.5 g of 3,4-difluoro-2-methoxy-N-(trifluoroacetyl)aniline (XI) as pale brown needles.

Mass Spectrum: m/e 255 ($M^+$), 186 ($M^+$-$CF_3$) and 158 ($M^+$-$COCF_3$).

Step (C2)
3,4-difluoro-N-(2-fluoroethyl)-2-methoxy-N-(trifluoroacetyl)aniline (XII, $R^{9'}$=2-fluoroethyl)

2.44 g (0.018 mole) of potassium carbonate, a catalytic amount of potassium iodide and 1.80 g (0.014 mole) of 2-fluoroethyl bromide were added to a solution of 3.00 g (0.012 mole) of 3,4-difluoro-2-methoxy-N-(trifluoroacetyl)aniline (XI) [prepared as described in Step (C1) above] dissolved in 50 ml of dimethylformamide. The mixture was then stirred at 65° C. for 5 hours. At the end of this time, the solvent was distilled off from the mixture under reduced pressure. The residue was extracted with ethyl acetate and purified by column chromatography through silica gel eluted with toluene, to give 0.69 g of 3,4-difluoro-N-(2-fluoroethyl)-2-methoxy-N-(trifluoroacetyl)aniline (XII, $R^{9'}$=2-fluoroethyl) as a colorless oil.

Mass Spectrum: m/e 301 ($M^+$), 268 ($M^+$-$CH_2F$) and 232 ($M^+$-$CF_3$).

Step (C3)
3,4-Difluoro-N-(2-fluoroethyl)-2-methoxyaniline (XIII, $R^{9'}$=2-fluoroethyl)

The whole of the oil obtained as described in step (C2) was dissolved in 80% aqueous methanol containing 0.25 g (0.0046 mole) of potassium hydroxide, and the solution was then allowed to stand at room temperature for 5 hours, after which the solvent was removed by evaporation under reduced pressure. The residue was extracted with toluene to give 0.45 g of 3,4-difluoro-N-(2-fluoroethyl)-2-methoxyaniline (XIII, $R^{9'}$=2-fluoroethyl) as a pale brown oil.

Mass Spectrum: m/e 205 ($M^+$), 190 ($M^+$-$CH_3$) and 172 ($M^+$-$CH_2F$).

Steps (C4)+(C5)
6,7-difluoro-1-(2-fluoroethyl)-8-methoxy-1,4-dihydro-4-oxoquinoline-3-carboxylate (X, $R^{9'}$=2-fluoroethyl)

A mixture of the whole (0.0022 mole) of the 3,4-difluoro-N-(2-fluoroethyl)-2-methoxyaniline prepared as described in step (C3) and 0.57 g (0.0026 mole) of diethyl ethoxymethylenemalonate was heated at 140°–150° C. for 6 hours, after which it was allowed to cool to room temperature. 2 ml of acetic anhydride and 1 ml of concentrated sulfuric acid were added in that order to the mixture, and it was then allowed to stand at room temperature. The reaction mixture was then poured into ice-water to precipitate crystals, which were collected by filtration to give 0.18 g of ethyl 6,7-difluoro-1-(2-fluoroethyl)-8-methoxy-1,4-dihydro-4-oxoquinoline-3-carboxylate (X, $R^{9'}$=2-fluoroethyl) as colorless crystals.

Mass Spectrum: m/e 329 ($M^+$), 284 ($M^+$-$OC_2H_5$) and 257 ($M^+$-$CH_2$=$CH_2$—$CO_2$).

Step (C6)
6,7-difluoro-1-(2-fluoroethyl)-8-methoxy-1,4-dihydro-4-oxoquinoline-3-carboxylic acid (IIa, $R^{9'}$=2-fluoroethyl)

5 ml of a 4% w/v aqueous solution of sodium hydroxide were added to a solution of the whole (0.0005 mole) of the ethyl 6,7-difluoro-1-(2-fluoroethyl)-8-methoxy-1,4-dihydro-4-oxoquinoline-3-carboxylate (X, $R^{9'}$=2-fluoroethyl) prepared as described in Step (C5) dissolved in 15 ml of methanol. The mixture was then allowed to stand at room temperature for 5 hours, after which it was acidified by adding concentrated hydrochloric acid to precipitate crystals. These crystals were collected by filtration to give 0.11 g of 6,7-difluoro-1-(2-fluoroethyl)-8-methoxy-1,4-dihydro-4-oxoquinoline-3-carboxylic acid (IIa, $R^{9'}$=2-fluoroethyl) as a colorless powder.

Mass Spectrum: m/e 301 ($M^+$) and 257 ($M^+$-$CO_2$).

PREPARATION 16

Ethyl 6,7-difluoro-1-ethyl-8-methoxy-1,4-dihydro-4-oxoquinoline-3-carboxylate (X, $R^{9'}$=ethyl)

Step (C2)
3,4-difluoro-N-ethyl-2-methoxy-N-(trifluoroacetyl)aniline (XII, $R^{9'}$=ethyl)

5.66 g (0.041 mole) of potassium carbonate and 6.39 g (0.041 mole) of ethyl iodide were added to a solution of 7.0 g (0.027 mole) of 3,4-difluoro-2-methoxy-N-(trifluoroacetyl)aniline (XI) [prepared as described in Preparation 15 (C1)] dissolved in 130 ml of dimethylformamide. The mixture was then stirred at 70° C. for 5 hours, after which the solvent was distilled off under reduced pressure. The residue was extracted with ethyl acetate, and then subjected to column chromatography through silica gel eluted with toluene, to give 7.6 g of 3,4-difluoro-N-ethyl-2-methoxy-N-(trifluoroacetyl)aniline (XII, $R^{9'}$=ethyl) as a reddish-brown oil.

Mass Spectrum: m/e 283 ($M^+$) and 214 ($M^+$-$CF_3$).

Step (C3) 3,4-difluoro-N-ethyl-2-methoxyaniline (XIII, $R^{9'}$=ethyl)

The whole of the oil obtained as described in step (C2) above was dissolved in 80% aqueous methanol containing 3.4 g (0.060 mole) of potassium hydroxide, and the solution was allowed to stand at room temperature for 5 hours. The solvent was then stripped from the reaction mixture by evaporation under reduced pressure, and the residue was extracted with toluene. The toluene was then removed from the extract by evaporation under reduced pressure, to give 5.5 g of 3,4-difluoro-N-ethyl-2-methoxyaniline (XIII, $R^{9'}$=ethyl) as a reddish brown oil.

Mass Spectrum: m/e 187 ($M^+$) and 172 ($M^+$-$CH_3$).

Steps (C4)+(C5) ethyl 6,7-difluoro-1-ethyl-8-methoxy-1,4-dihydro-4-oxoquinoline-3-carboxylate (X, R$^{9'}$=ethyl)

A mixture of 4.0 g (0.021 mole) of the 3,4-difluoro-N-ethyl-2-methoxyaniline (XIII) [prepared as described in Step (C3) above] and 5.54 g (0.026 mole) of diethyl ethoxymethylenemalonate was heated at 150°-160° C. for 9 hours. The mixture was then allowed to cool to room temperature, and 42 ml of acetic anhydride and 18 ml of concentrated sulfuric acid were then added, in that order. The reaction mixture was poured into ice-water to precipitate crystals, which were collected by filtration to give 2.09 g of ethyl 6,7-difluoro-1-ethyl-8-methoxy-1,4-dihydro-4-oxoquinoline-3-carboxylate (X, R$^{9'}$=ethyl) as a colorless powder.

Mass Spectrum: m/e 311 (M+) and 239 (M+-CH$_2$=CH—CO$_2$)

PREPARATION 17

6,7-Difluoro-8-methoxy-1-methylamino-1,4-dihydro-4-oxoquinoline-3-carboxylic acid (IIb, R$^{10}$=methyl)

Step (D1) ethyl 1-amino-6,7-difluoro-8-methoxy-1,4-dihydro-4-oxoquinoline-3-carboxylate (XV)

1.10 g (0.008 mole) of potassium carbonate was added to a solution of 1.13 g (0.004 mole) of ethyl 6,7-difluoro-4-hydroxy-8-methoxyquinoline-3-carboxylate (IX) [prepared as described in Preparation 14 (B3)] in 20 ml of dimethylformamide and the mixture was stirred at room temperature for 3 hours. 0.81 g (0.0041 mole) of O-(2,4-dinitrophenyl)hydroxylamine was then added, and the mixture was stirred at room temperature for 6 hours. At the end of this time, the solvent was distilled from the reaction mixture under reduced pressure. The residue was washed, in turn, with water and with ethanol. The solid produced was extracted with chloroform, and the solvent was stripped from the extract, to give 0.62 g of ethyl 1-amino-6,7-difluoro-8-methoxy-1,4-dihydro-4-oxoquinoline-3-carboxylate (XV) as an ocherous powder.

Mass Spectrum: m/e 298 (M+),
Infrared Absorption Spectrum (KBr) $\nu_{max}$ cm$^{-1}$:
Nuclear Magnetic Resonance Spectrum (CDCl$_3$) δppm: 1.38 (3H, triplet); 4.23 (3H, doublet); 4.32 (2H, quartet); 6.01 (2H, singlet); 7.88 (1H, doublet of doublets); 8.48 (1H, singlet).

Step (D2) ethyl 6,7-difluoro-1-(formylamino)-8-methoxy-1,4-dihydro-4-oxoquinoline-3-carboxylate (XVI)

A solution was prepared by dropping 1.5 ml (0.04 mole) of formic acid onto 3.8 ml (0.04 mole) of acetic anhydride, whilst ice-cooling, and then stirring the mixture at the same temperature for 15 minutes and then at 50° C. for 15 minutes. This solution was added dropwise to a solution of 0.6 g (0.002 mole) of ethyl 1-amino-6,7-difluoro-8-methoxy-1,4-dihydro-4-oxoquinoline-3-carboxylate (XV) [prepared as described in Step (D1) above] dissolved in 4.2 ml (0.11 mole) of formic acid, whilst ice-cooling. The mixture was stirred at room temperature for 9 hours. At the end of this time, the solvent was distilled off under reduced pressure from the mixture. The residue was washed, in turn, with water and diethyl ether, to give 0.6 g of ethyl 6,7-difluoro-1-(formylamino)-8-methoxy-1,4-dihydro-4-oxoquinoline-3-carboxylate (XVI) as a pale yellow powder.

Infrared Absorption Spectrum (KBr) $\nu_{max}$ cm$^{-1}$: 1700-1725 and 1614.
Nuclear Magnetic Resonance Spectrum (hexadeuterated dimethyl sulfoxide-CDCl$_3$) δppm: 1.39 (3H, triplet); 3.98 (3H, singlet); 4.35 (2H, quartet); 7.97 (1H, doublet of doublets); 8.38 (1H, broad singlet); 9.41 (2H, broad singlet).

Step (D3) ethyl 6,7-difluoro-1-(N-formylmethylamino)-8-methoxy-1,4-dihydro-4-oxoquinoline-3-carboxylate (XVII, R$^{10}$=methyl)

The whole (0.0018 mole) of the ethyl 6,7-difluoro-1-(formylamino)-8-methoxy-1,4-dihydro-4-oxoquinoline-3-carboxylate (XVI) [prepared as described in Step (D2) above] was dissolved in 8 ml of dimethylformamide. 0.51 g (0.0037 mole) of potassium carbonate and 0.78 g (0.0052 mole) of methyl iodide were then added to the solution, and the mixture was stirred at room temperature for 3 hours. At the end of this time, the solvent was distilled from the mixture under reduced pressure. The residue was extracted with chloroform, and the chloroform extract was washed with water, dried and concentrated by evaporation under reduced pressure to give 0.5 g of ethyl 6,7-difluoro-1-(N-formylmethylamino)-8-methoxy-1,4-dihydro-4-oxoquinoline-3-carboxylate (XVII, R$^{10}$=methyl) as a colorless powder.

Mass Spectrum: m/e 340 (M+) and 268 (M+-CH$_2$=CH—CO$_2$).

Step (D4) 6,7-difluoro-8-methoxy-1-(methylamino)-1,4-dihydro-4-oxoquinoline-3-carboxylic acid (IIb, R$^{10}$=methyl)

4.5 ml (0.0045 mole) of a 1N aqueous solution of sodium hydroxide were added to a solution of the whole (0.0015 mole) of the ethyl 6,7-difluoro-1-(N-formylmethylamino)-8-methoxy-1,4-dihydro-4-oxoquinoline-3-carboxylate (XVII, R$^{10}$=methyl) [prepared as described in Step (D3) above] dissolved in 10 ml of ethanol, and the mixture was stirred at room temperature for 2 hours. At the end of this time, addition of acetic acid gave rise to crystals, which were collected by filtration to give 0.35 g of 6,7-difluoro-8-methoxy-1-(methylamino)-1,4-dihydro-4-oxoquinoline-3-carboxylic acid (IIb, R$^{10}$=methyl) as a colorless powder.

Mass Spectrum: m/e 284 (M+) and 240 (M+-CO$_2$).
Nuclear Magnetic Resonance Spectrum (CDCl$_3$) δppm: 2.90 (3H, doublet); 4.30 (3H, doublet); 6.69 (1H, quartet); 8.10 (1H, doublet of doublets); 8.83 (1H, singlet); 14.33 (1H, singlet).

PREPARATION 18 trans-3-Amino-4-methoxypyrrolidine dihydrochloride (1) 3.7 g (0.02 mole) of 1-t-butoxycarbonyl-3,4-epoxypyrrolidine (prepared as described in Preparation 8) were dissolved in 15 ml of ethanol. 7.88 g (0.04 mole) of dibenzylamine were added to the solution, and the mixture was heated under reflux for 10 hours. At the end of this time, the solvent was removed by evaporation under reduced pressure, and the residue was subjected to column chromatography through silica gel, eluted with a 12:88 by volume mixture of ethyl acetate and toluene, to give 1.21 g of 1-t-butoxycarbonyl-3-dibenzylamino-4-hydroxypyrrolidine as a pale yellow oil.

Mass Spectrum (CI): m/e 383 (M+ +1).

Infrared Absorption Spectrum (Capillary) $\nu_{max}$ cm$^{-1}$: 3420, 1690, 1670, 1420 and 1175.

(2) 0.19 g (0.0047 mole) of sodium hydride (as a 60% w/w dispersion in mineral oil) and 0.89 g (0.0063 mole) of methyl iodide were added, in that order, to a solution of 1.2 g (0.0031 mole) of 1-t-butoxycarbonyl-3-dibenzylamino-4-hydroxypyrrolidine [prepared as described in Step (1) above] dissolved in 10 ml of tetrahydrofuran. The mixture was then stirred at room temperature for 5 hours. At the end of this time, water was added to the reaction mixture, which was then extracted with ethyl acetate. The ethyl acetate extract was washed with water, dried and concentrated by evaporation under reduced pressure. The residue was subjected to column chromatography through silica gel, eluted with a 5:95 by volume mixture of ethyl acetate and toluene, to give 0.99 g of 1-t-butoxycarbonyl-3-dibenzylamino-4-methoxypyrrolidine as a colorless oil.

Mass Spectrum: m/e 396 (M+), 340 [M+-$CH_2$=$C(CH_3)_2$], 305 (M+-$CH_2$Ph) and 296 [M+-$CO_2$—$CH_2$=$C(CH_3)_2$].

Infrared Absorption Spectrum (Capillary) $\nu_{max}$ cm$^{-1}$: 1690, 1390~1410, 1170 and 1100.

(3) 0.13 g of 20% w/w palladium-on-carbon was added to a solution of 0.99 g (0.0025 mole) of 1-t-butoxycarbonyl-3-dibenzylamino-4-methoxypyrrolidine dissolved in 15 ml of ethanol, and the mixture was stirred vigorously at 50° C. for 4 hours in an atmosphere of hydrogen. The catalyst was filtered off from the reaction mixture, after which the filtrate was concentrated by evaporation under reduced pressure, to give 0.44 g of 3-amino-1-t-butoxycarbonyl-4-methoxypyrrolidine as a colorless oil.

Mass Spectrum (CI) m/e 217 (M+ +1); (EI) m/e 184 (M+-$CH_3OH$) and 160 (M+-$CH_2$=$C(CH_3)_2$).

Infrared Absorption Spectrum (Capillary) $\nu_{max}$ cm$^{-1}$: 3370, 3300, 1660~1690, 1400, 1160 and 1100.

(4) 6.3 ml of 6N aqueous hydrochloric acid were added to a solution of 0.4 g (0.0019 mole) of 3-amino-1-t-butoxycarbonyl-4-methoxypyrrolidine [prepared as described in Step (3) above] dissolved in 20 ml of ethanol, and the mixture was heated under reflux for 1.5 hours, after which the solvent was removed by evaporation under reduced pressure. The residue was washed with a 1:9 by volume mixture of ethanol and ethyl acetate to give 0.34 g of trans-3-amino-4-methoxypyrrolidine dihydrochloride as a colorless powder, melting at 248°~258° C. (with decomposition).

Mass Spectrum (CI): m/e 117 (M+ +1); (EI): m/e 99 (M+-$NH_3$) and 84 (M+-$CH_3OH$).

$^{13}C$ Nuclear Magnetic Resonance Spectrum ($D_2O$) $\delta$ppm: 50.1 ($C_2$); 51.1 ($C_5$); 56.0 ($C_3$); 60.0 (—O$\underline{C}H_3$); 84.2 ($C_4$).

PREPARATION 19

3-Aminomethyl-3-hydroxypyrrolidine (1) A solution of 27.3 g (0.143 mole) of 1-benzyl-3-hydroxymethylpyrrolidine [cf. J. Org. Chem., 26, 1519 (1961)] dissolved in 600 ml of ethanol was stirred vigorously at 70° C. for 3 hours in the presence of 9.15 g of 20% w/w palladium-on-carbon whilst bubbling hydrogen through the solution at atmospheric pressure. At the end of this time, the catalyst was filtered off from the reaction mixture, and the solvent was removed by distillation under reduced pressure to give 14.7 g of 3-hydroxymethylpyrrolidine as a pale yellow oil.

(2) 14.7 g (0.143 mole) of 3-hydroxymethylpyrrolidine [prepared as described in Step (1) above] was dissolved in 150 ml of methylene chloride. A solution of 32.7 g (0.150 mole) of di-t-butyl dicarbonate dissolved in 40 ml of methylene chloride was added dropwise to the solution, whilst ice-cooling. The mixture was then stirred at room temperature for 7 hours, after which the solvent was removed by distillation under reduced pressure to give 29.5 g of 1-t-butoxycarbonyl-3-hydroxymethylpyrrolidine as a brown oil.

Mass Spectrum: m/e 201 (M+), 145 [M+-$CH_2$=$C(CH_3)_2$], 128 [M+-$CH_2$=$C(CH_3)_2$ & —OH] and 57 ($C_4H_9^+$).

Infrared Absorption Spectrum (Capillary) $\nu_{max}$ cm$^{-1}$: 3400, 1690, 1680, 1420, 1175 and 1140.

(3) 30.0 g (0.157 mole) of p-toluenesulfonyl chloride were added to a solution of 29.5 g (0.143 mole) of 1-t-butoxycarbonyl-3-hydroxymethylpyrrolidine [prepared as described in Step (2) above] dissolved in 500 ml of pyridine. The mixture was then stirred for 5 hours whilst ice-cooling, after which it was stirred at room temperature overnight. The reaction mixture was poured into 1 liter of water and then extracted with ethyl acetate. The extract was washed with water, dried and concentrated under by evaporation reduced pressure. The residue was subjected to column chromatography through silica gel eluted with a 1:4 by volume mixture of ethyl acetate and toluene, to give 36.6 g of 1-t-butoxycarbonyl-3-(p-toluenesulfonyloxymethyl)-pyrrolidine as a pale brown oil, which gradually crystallized.

Infrared Absorption Spectrum (Capillary) $\nu_{max}$ cm$^{-1}$: 1690, 1390~1420, 1365, 1175, 960 and 820.

(4) 2.24 g (0.02 mole) of potassium t-butoxide were added to a solution of 3.55 g (0.01 mole) of 1-t-butoxycarbonyl-3-(p-toluenesulfonyloxymethyl)pyrrolidine [prepared as described in Step (3) above] dissolved in 50 ml of tetrahydrofuran. The mixture was then stirred at room temperature for 3 hours, after which it was poured into water and then extracted with ethyl acetate. The ethyl acetate extract was washed with water, dried and concentrated by evaporation under reduced pressure. The residue was subjected to column chromatography through silica gel eluted with a 5:95 by volume mixture of ethyl acetate and toluene, to give 0.79 g of 1-t-butoxycarbonyl-3-methylenepyrrolidine as a pale yellow liquid.

Mass Spectrum: m/e 183 (M+) and 57 ($C_4H_9^+$).

Infrared Absorption Spectrum (Capillary) $\nu_{max}$ cm$^{-1}$: 1690~1710, 1395~1415, 1170, 1110 and 890.

Nuclear Magnetic Resonance Spectrum (CDCl$_3$) $\delta$ppm: 1.47 (9H, singlet); 2.54 (2H, triplet); 3.45 (2H, triplet); 3.92 (2H, broad); 4.97 (2H, broad).

(5) 3.54 g (0.0175 mole) of 85% m-chloroperbenzoic acid were added to a solution of 2.67 g (0.0146 mole) of 1-t-butoxycarbonyl-3-methylenepyrrolidine [prepared as described in Step (4) above] in 20 ml of chloroform, whilst ice-cooling, and the mixture was stirred at the same temperature for 6 hours and then stirred at room temperature overnight. At the end of this time, 1.8 g (0.073 mole) of 70% m-chloroperbenzoic acid were added, and the mixture was stirred at room temperature for 12 hours. At the end of this time, the mixture was extracted with toluene. The toluene extract was washed, in turn, with an aqueous solution of sodium bicarbonate, with an aqueous solution of sodium thiosulfate and with water, in that order, after which it was dried and concentrated by evaporation under reduced pressure. The residue was subjected to column chromatography through silica gel eluted with a 1:9 by volume mixture of ethyl acetate and toluene, to give 1.77 g of 1-t-butoxycarbonyl-3-(1,2-epoxyethyl)pyrrolidine as a colorless liquid.

Mass Spectrum: m/e 199 ($M^+$) and 57 ($C_4H_9^+$).

Infrared Absorption Spectrum (Capillary) $\nu_{max}$ $cm^{-1}$: 1690, 1400~1410, 1170~1180 and 1110.

(6) 2.0 of 1-t-butoxycarbonyl-3-(1,2-epoxyethyl)pyrrolidine [prepared as described in Step (5) above] were placed in a 100 ml stainless autoclave, to which 50 ml of liquid ammonia were then added. The mixture was stirred at 100° C. for 9.5 hours under pressure. At the end of this time, excess ammonia was evaporated off, and the residue was subjected to column chromatography through silica gel eluted with a 1:2 by volume mixture of methanol and ethyl acetate, to give 2.10 g of 3-aminomethyl-1-t-butoxycarbonyl-3-hydroxypyrrolidine as a brown oil.

Infrared Absorption Spectrum (Capillary) $\nu_{max}$ $cm^{-1}$: 2500~3700, 1650~1670 and 1400~1430.

Nuclear Magnetic Resonance Spectrum ($CDCl_3$) δppm: 1.46 (9H, singlet); 1.55~2.02 (5H, multiplet); 2.81 (2H, singlet); 3.14~3.62 (4H, multiplet).

(7) 32 ml of 6N aqueous hydrochloric acid were added to a solution of 2.1 g (0.0097 mole) of 3-aminomethyl-1-t-butoxycarbonyl-3-hydroxypyrrolidine [prepared as described in Step (6) above] dissolved in 90 ml of ethanol, and the mixture was heated under reflux for 1 hour. Evaporation of the mixture to dryness under reduced pressure gave 1.54 g of a pale brown hygroscopic solid, which was then dissolved in 10 ml of water. 0.88 g (0.016 mole) of sodium methoxide were added to the resulting solution, after which the solvent was distilled off and the residue was washed with a 1:1 by volume mixture of ethanol and ethyl acetate. The washings were concentrated by evaporation under reduced pressure, to give 0.93 g of 3-aminomethyl-3-hydroxypyrrolidine as a brown oil.

Mass Spectrum (CI): m/e 117 ($M^+ +1$), (EI): m/e 99 ($M^+$-$NH_3$) and 84 ($M^+$-$CH_3OH$).

PREPARATION 20

3-Amino-4-methylpyrrolidine dihydrochloride (1) 350 ml (2.8 moles) of ethyl methacrylate were added to a solution of 150 g (1.4 moles) of benzylamine dissolved in 400 ml of ethanol. The mixture was heated under reflux for 4 hours, and then 175 ml (1.4 mole) of ethyl methacrylate were added to it, after which it was heated under reflux for 24 hours. The solvent and the unreacted materials were then removed from the mixture by evaporation under reduced pressure. The residue was purified by column chromatography through silica gel eluted with a 1:1 by volume mixture of ethyl acetate and toluene, to afford 98.0 g of N-(2-ethoxycarbonylpropyl)benzylamine as a red oil.

(2) 88.4 g (0.53 mole) of ethyl bromoacetate were added to a solution of 98.0 g (0.44 mole) of N-(2-ethoxycarbonylpropyl)benzylamine [prepared as described in Step (1) above] dissolved in 200 ml of ethanol, and the mixture was heated under reflux for 2 hours. The reaction mixture was then poured into 500 ml of ice-water and made alkaline by the addition of a 50% w/v aqueous solution of sodium hydroxide. It was then extracted with ethyl acetate. The ethyl acetate extract was washed, in turn, with a 1N aqueous solution of sodium hydroxide and with water and dried. It was then freed from the solvent by evaporation under reduced pressure. The residue was purified by column chromatography through silica gel eluted with a 1:9 by volume mixture of ethyl acetate and toluene, to give 83.0 g of N-ethoxycarbonylmethyl-N-(2-ethoxycarbonylpropyl)-benzylamine as a pale yellow oil.

(3) 60.2 g (0.196 mole) of N-ethoxycarbonylmethyl-N-(2-ethoxycarbonylpropyl)benzylamine [prepared as described in Step (2) above] were added dropwise to a suspension of 24.2 g (0.22 mole) of potassium t-butoxide in 300 ml of toluene over a period of 3 hours, whilst keeping the temperature below 6° C. The mixture was then stirred at the same temperature for 3 hours, after which 13 g of acetic acid were added to it. The toluene layer was separated, washed with water and dried, and the solvent was removed by evaporation under reduced pressure, to give 48.0 g of 1-benzyl-4-ethoxycarbonyl-4-methyl-3-pyrrolidone as a red oil.

Mass Spectrum (CI): m/e 262 ($M^+ +1$).

(4) A mixture of 48.0 g (0.184 mole) of 1-benzyl-4-ethoxycarbonyl-4-methyl-3-pyrrolidone [prepared as described in Step (3) above] and 80 ml of concentrated hydrochloric acid was heated under reflux for 24 hours. The reaction mixture was then filtered, and the filtrate was concentrated by evaporation under reduced pressure. The residue was diluted with water and made alkaline by adding a 50% w/v aqueous solution of sodium hydroxide to pH 10, after which it was extracted with diethyl ether. The diethyl ether extract was dried and the solvent was then distilled from the extract under reduced pressure. The residue was purified by column chromatography through silica gel eluted with a 2.5:7.5 by volume mixture of ethyl acetate and toluene, to give 31.7 g of 1-benzyl-4-methyl-3-pyrrolidone as a red oil.

(5) A solution of 31.7 g (0.168 mole) of 1-benzyl-4-methyl-3-pyrrolidone [prepared as described in Step (4) above] dissolved in 200 ml of ethanol was added dropwise to a solution of 59.4 g (0.79 mole) of hydroxylamine hydrochloride dissolved in 200 ml of water over a period of 1 hour, whilst keeping the temperature at 20° to 25° C. 62.1 g (0.45 mole) of potassium carbonate were then added, and the mixture was stirred at room temperature overnight, after which it was diluted with 100 ml of water. The aqueous solution was extracted with chloroform, and the chloroform extract was washed with water, dried and concentrated by evaporation under reduced pressure, to give 36.9 g of 1-benzyl-3-(hydroxyimino)-4-methylpyrrolidine as brown crystals.

(6) 90 ml of a 20% w/v aqueous solution of sodium hydroxide were added to a solution of 12 g (0.059 mole) of 1-benzyl-3-(hydroxyimino)-4-methylpyrrolidine [prepared as described in Step (5) above] dissolved in 100 ml of ethanol. 23.9 g of Raney nickel (about 50%) were gradually added to the mixture, whilst vigorously stirring it. After the reaction mixture had been stirred for 3 hours, it was filtered. The upper layer of the filtrate was separated and concentrated by evaporation under reduced pressure. The residue was purified by column chromatography through silica gel eluted with methanol, to give 80 g of 1-benzyl-3-amino-4-methylpyrrolidine as a pale yellow liquid.

(7) A solution of 8.0 g (0.042 mole) of 1-benzyl-3-amino-4-methylpyrrolidine [prepared as described in Step (6) above] dissolved in 40 ml of ethanol was placed in a 100 ml autoclave and hydrogenated in the presence of 0.8 g of 5% w/w palladium-on-carbon at 80° C., and under an initial pressure of hydrogen of 40 kg/cm² for 3 hours. At the end of this time, the mixture was filtered to remove the catalyst, 10 ml of concentrated hydrochloric acid were added to the filtrate, and then the mixture was concentrated by evaporation under reduced pressure. Adding ethanol to the residue precipitated crystals, which were collected by filtration to give 4.8 g of 3-amino-4-methylpyrrolidine dihydrochloride as hygroscopic, pale-reddish crystals.

The $^{13}C$ nuclear magnetic resonance spectrum showed a mixture of the cis isomer with the trans isomer.

$^{13}C$ Nuclear Magnetic Resonance Spectrum: ($D_2O$) δppm: 13.0, 16.8 (—$CH_3$); 37.2, 39.8 ($C_4$); 50.5, 51.0 ($C_5$); 52.6, 53.2 ($C_2$); 54.5, 57.5 ($C_3$).

Mass spectrum: m/e 100 ($M^+$) and 36 (HCl).

BIOLOGICAL ACTIVITY

The antibacterial activities of a number of compounds of the invention were investigated against a wide variety of bacteria, both Gram-positive and Gram-negative, and the results are shown in the following Tables 5 and 6 in terms of their minimal inhibitory concentrations (μg/ml)

For convenience of use, all the compounds were investigated in the form of their hydrochlorides, but this would not have any substantial effect upon the results and essentially the same pattern of results would be expected from the free amines or from other conventional salts or esters thereof.

By way of comparison, results are also given for the known compound, Norfloxacin.

Each compound of the invention is, for brevity, identified by the number of one of the foregoing Examples which illustrates its prepartion.

TABLE 5

| Microorganism | | Compound of Ex. No. | | |
|---|---|---|---|---|
| | | 1 | 2 | 4 |
| Staphylococcus | 209P | 0.1 | 0.1 | 0.05 |
| aureus | 56 | 0.1 | 0.1 | 0.05 |
| | 535 | 0.4 | 0.1 | 0.1 |
| Enterococcus faecalis | 681 | 0.2 | 0.2 | 0.1 |
| Escherichia | NIHJ | 0.02 | 0.02 | 0.02 |
| coli | 609 | 0.8 | 0.8 | 0.4 |
| Salmonella enteritidis | | 0.02 | ≦0.01 | 0.02 |
| Klebsiella | 806 | 0.1 | 0.1 | 0.1 |
| pneumoniae | 846 | 0.1 | 0.05 | 0.05 |
| Enterobacter cloacae | 963 | 0.1 | 0.1 | 0.1 |
| Serratia marcescens | 1184 | 0.2 | 0.2 | 0.2 |
| Proteus vulqaris | 1420 | ≦0.01 | ≦0.01 | ≦0.01 |
| Morqanella | 1510 | 0.02 | 0.05 | 0.1 |

TABLE 5-continued

| Microorganism | | Compound of Ex. No. | | |
|---|---|---|---|---|
| | | 1 | 2 | 4 |
| morqanii | | | | |
| Pseudomonas aeruqinosa | 1001 | 0.8 | 0.8 | 0.4 |

TABLE 6

| Microorganism | | Compound of Ex. No. | | | Norfloxacin |
|---|---|---|---|---|---|
| | | 22 | 23 | 71 | |
| Staphylococcus | 209P | 0.05 | <0.01 | 0.02 | 0.2 |
| aureus | 56 | 0.05 | ≦0.01 | 0.02 | 0.4 |
| | 535 | 0.2 | 0.05 | 0.05 | 6.2 |
| Enterococcus faecalis | 681 | 0.2 | 0.1 | 0.1 | 3.1 |
| Escherichia | NIHJ | 0.02 | 0.05 | 0.05 | 0.2 |
| coli | 609 | 0.4 | 0.4 | 0.4 | 3.1 |
| Salmonella enteritidis | | ≦0.01 | 0.05 | 0.02 | 0.1 |
| Klebsiella | 806 | 0.1 | 0.1 | 0.05 | 0.4 |
| pneumoniae | 846 | 0.05 | 0.05 | 0.02 | 0.4 |
| Enterobacter cloacae | 963 | 0.05 | 0.1 | 0.1 | 0.4 |
| Serratia marcescens | 1184 | 0.2 | 0.2 | 0.2 | 0.2 |
| Proteus vulqaris | 1420 | ≦0.01 | ≦0.01 | ≦0.01 | 0.02 |
| Morganella morganii | 1510 | 0.05 | 0.1 | 0.1 | 0.05 |
| Pseudomonas aeruqinosa | 1001 | 0.8 | 0.8 | 0.8 | 0.8 |

We claim:

1. A compound which is selected from the group consisting of 1-cyclopropyl-6-fluoro-8-methoxy-7-[4-(2-hydroxyethyl)-1-piperazinyl]-1,4-dihydro-4-oxoquinoline-3-carboxylic acid and pharmaceutically acceptable salts thereof.

2. The compound of claim 1 which is 1-cyclopropyl-6-fluoro-8-methoxy-7-[4-(2-hydroxyethyl)-1-piperazinyl]-1,4-dihydro-4-oxoquinoline-3-carboxylic acid.

3. A composition for the treatment of bacterial infections, comprising an effective amount of an antibacterial agent in combination with a pharmaceutically acceptable carrier or diluent, wherein the antibacterial agent is selected from the group consisting of 1-cyclopropyl-6-fluoro-8-methoxy-7-[4-(2-hydroxyethyl)-1-piperazinyl]-1,4-dihydro-4-oxoquinoline-3-carboxylic acid and pharmaceutically acceptable salts, esters and amides thereof.

4. A method for the treatment of bacterial infection comprising administering an amount of an antibacterial agent to an animal sufficient of exert an antibacterial effect, wherein said antibacterial agent is selected from the group consisting of 1-cyclopropyl-6-fluoro-8-methoxy-7-[4-(2-hydroxyethyl)-1-piperazinyl]-1,4-dihydro-4-oxoquinoline-3-carboxylic acid and pharmaceutically acceptable salts, esters and amides thereof.

* * * * *